US008993231B2

(12) United States Patent
Claudio et al.

(10) Patent No.: US 8,993,231 B2
(45) Date of Patent: Mar. 31, 2015

(54) METHODS FOR STEM CELL PRODUCTION AND THERAPY

(75) Inventors: Pier Paolo Claudio, Huntington, WV (US); Jagan V. Valluri, Huntington, WV (US)

(73) Assignee: Marshall University Research Corporation, Huntington, WV (US)

(*) Notice: Subject to any disclaimer, the term of this patent is extended or adjusted under 35 U.S.C. 154(b) by 360 days.

(21) Appl. No.: 12/405,944

(22) Filed: Mar. 17, 2009

(65) Prior Publication Data

US 2010/0062435 A1    Mar. 11, 2010

Related U.S. Application Data

(60) Provisional application No. 61/069,886, filed on Mar. 18, 2008, provisional application No. 61/136,496, filed on Sep. 9, 2008.

(51) Int. Cl.
| | | |
|---|---|---|
| *C12Q 1/68* | (2006.01) | |
| *C12N 5/00* | (2006.01) | |
| *C12Q 1/48* | (2006.01) | |
| *C12N 5/095* | (2010.01) | |

(52) U.S. Cl.
CPC .......... *C12N 5/0695* (2013.01); *C12N 2500/36* (2013.01); *C12N 2525/00* (2013.01)
USPC ............... 435/6.1; 435/7.4; 435/15; 435/375; 435/394

(58) Field of Classification Search
None
See application file for complete search history.

(56) References Cited

U.S. PATENT DOCUMENTS

| | | | |
|---|---|---|---|
| 4,366,241 A | 12/1982 | Tom et al. | |
| 4,376,110 A | 3/1983 | David et al. | |
| 4,517,288 A | 5/1985 | Giegel et al. | |
| 4,837,168 A | 6/1989 | de Jaeger et al. | |
| 5,153,132 A | 10/1992 | Goodwin et al. | |
| 5,153,133 A | 10/1992 | Schwarz et al. | |
| 5,155,034 A | 10/1992 | Wolf et al. | |
| 5,155,035 A | 10/1992 | Schwarz et al. | |
| 5,308,764 A | 5/1994 | Goodwin et al. | |
| 5,496,722 A | 3/1996 | Goodwin et al. | |
| 5,523,228 A | 6/1996 | Ingram et al. | |
| 5,627,021 A | 5/1997 | Goodwin et al. | |
| 5,846,807 A | 12/1998 | Goodwin | |
| 5,851,816 A | 12/1998 | Goodwin et al. | |
| 5,858,783 A | 1/1999 | Goodwin et al. | |
| 6,001,642 A | 12/1999 | Tsao | |
| 6,001,643 A | 12/1999 | Spaulding | |
| 6,177,674 B1 | 1/2001 | Rutt et al. | |
| 6,485,963 B1 | 11/2002 | Wolf et al. | |
| 6,673,597 B2 | 1/2004 | Wolf et al. | |
| 6,902,909 B2 | 6/2005 | Navran, Jr. et al. | |
| 7,179,217 B2 | 2/2007 | Goodwin et al. | |
| 2004/0042997 A1 | 3/2004 | Rudd | |
| 2004/0043009 A1 | 3/2004 | Rudd | |
| 2004/0044300 A1 | 3/2004 | Rudd | |
| 2004/0076605 A1 | 4/2004 | Rudd | |
| 2004/0076620 A1 | 4/2004 | Rudd | |
| 2004/0077985 A1 | 4/2004 | Rudd | |
| 2004/0265996 A1 | 12/2004 | Schwarz et al. | |
| 2006/0148078 A1 | 7/2006 | Gerecht-Nir et al. | |
| 2006/0188984 A1 | 8/2006 | Rudd | |
| 2006/0193836 A1 | 8/2006 | Rudd | |
| 2006/0193837 A1 | 8/2006 | Rudd | |
| 2006/0193838 A1 | 8/2006 | Rudd | |
| 2006/0193839 A1 | 8/2006 | Rudd | |

(Continued)

FOREIGN PATENT DOCUMENTS

| | | | |
|---|---|---|---|
| DE | EP 1 792 979 A1 * | 6/2007 | ............... C12N 5/06 |
| WO | WO 00/00586 A1 | 1/2000 | |

(Continued)

OTHER PUBLICATIONS

Select Define printout from www.dictionary.reference.com/browse/select, p. 1, dated Mar. 4, 2011.*

(Continued)

*Primary Examiner* — Karen Canella
(74) *Attorney, Agent, or Firm* — Stites & Harbison PLLC; Terry L. Wright

(57) ABSTRACT

The present invention relates to methods for rapidly expanding a stem cell population with or without culture supplements in simulated microgravity conditions. The present invention relates to methods for rapidly increasing the life span of stem cell populations without culture supplements in simulated microgravity conditions. The present invention also relates to methods for increasing the sensitivity of cancer stem cells to chemotherapeutic agents by culturing the cancer stem cells under microgravity conditions and in the presence of omega-3 fatty acids. The methods of the present invention can also be used to proliferate cancer cells by culturing them in the presence of omega-3 fatty acids. The present invention also relates to methods for testing the sensitivity of cancer cells and cancer stem cells to chemotherapeutic agents by culturing the cancer cells and cancer stem cells under microgravity conditions. The methods of the present invention can also be used to produce tissue for use in transplantation by culturing stem cells or cancer stem cells under microgravity conditions. The methods of the present invention can also be used to produce cellular factors and growth factors by culturing stem cells or cancer stem cells under microgravity conditions. The methods of the present invention can also be used to produce cellular factors and growth factors to promote differentiation of cancer stem cells under microgravity conditions.

34 Claims, 19 Drawing Sheets

(56) References Cited

U.S. PATENT DOCUMENTS

| | | |
|---|---|---|
| 2006/0228795 A1 | 10/2006 | Parker |
| 2006/0229487 A1 | 10/2006 | Goodwin et al. |
| 2006/0240550 A1 | 10/2006 | Goodwin et al. |
| 2007/0048253 A1 | 3/2007 | Goodwin et al. |
| 2007/0082328 A1 | 4/2007 | Rudd |
| 2007/0087324 A1 | 4/2007 | Rudd |
| 2007/0098699 A1 | 5/2007 | Rudd |
| 2007/0098704 A1 | 5/2007 | Rudd |
| 2007/0100195 A1 | 5/2007 | Goodwin et al. |
| 2007/0111306 A1 | 5/2007 | Salli et al. |
| 2007/0117087 A1 | 5/2007 | Rudd |
| 2007/0172466 A1 | 7/2007 | Rudd |
| 2007/0190520 A1 | 8/2007 | Wolf et al. |
| 2008/0044890 A1 | 2/2008 | Parker |
| 2008/0050348 A1 | 2/2008 | Rudd |
| 2008/0057042 A1 | 3/2008 | Rudd |
| 2008/0075700 A1 | 3/2008 | Wolf et al. |
| 2008/0075704 A1 | 3/2008 | Wolf et al. |

FOREIGN PATENT DOCUMENTS

| | | | |
|---|---|---|---|
| WO | WO 2004/050826 A2 | | 6/2004 |
| WO | WO 2005/007799 A2 | | 1/2005 |
| WO | WO2010/091226 | * | 8/2010 |

OTHER PUBLICATIONS

IMDM medium printout from http://products.invitrogen. com/ivgn/product/12440079, pp. 1-3, dated Mar. 4, 2011.*
Alvarez-Buylla, A., et al., "Identification of neural stem cells in the adult vertebrate brain," *Brain Research Bulletin* 57:751-758, Elsevier Science Inc., Amsterdam, The Netherlands (2002).
Colvin, G.A., et al., "Rhythmicity of Engraftment and Altered Cell Cycle Kinetics of Cytokine-Cultured Murine Marrow in Simulated Microgravity Compared with Static Cultures," *In Vitro Cell. Dev. Biol.—Animal* 38:343-351, Society for In Vitro Biology, St. Louis, Missouri USA (2002).
Cong, Y. and Shay, J.W., "Actions of human telomerase beyond telomeres," *Cell Research* 18:725-732, Nature Publishing Group, New York NY USA (Jun. 2008).
Dutt, K., et al., "Generation of 3D Retina-Like Structures From a Human Retinal Cell Line in a NASA Bioreactor," *Cell Transplantation* 12:717-731, Cognizant Comm. Corp., Elmsford, NY USA (2003).
Gan, O.I., et al., "Differential Maintenance of Primitive Human SCID-Repopulating Cells, Clonogenic Progenitors, and Long-Term Culture-Initiating Cells After Incubation on Human Bone Marrow Stromal Cells," *Blood* 90:641-650, The American Society of Hematology, Washington, DC USA (1997).
Gerecht-Nir, S., et al., "Bioreactor Cultivation Enhances the Efficiency of Human Embryoid Body (hEB) Formation and Differentiation," *Biotechnology and Bioengineering* 86:493-502, Wiley Periodicals, Inc., Hoboken, NJ USA (2004).
Godara, P., et al., "Design of bioreactors for mesenchymal stem cell tissue engineering," *Journal of Chemical Technology and Biotechnology* 83:408-420, Society of Chemical Industry, London UK (Feb. 2008).
Gonda, S.R., and Spaulding, G.F., "Hydrofocusing Bioreactor for Three-Dimensional Cell Culture," NASA Tech Brief MSC-22538, Washington DC (2003).
Guidi, A., et al., Mechanobiologic Research in a Microgravity Environment Bioreactor, 53$^{rd}$ International Astronautical Congress of the International Astronautical Federation (IAF), Houston, TX, USA; Oct. 10-19, 2002; pp. 1-9.
Hahn, H., et al., "Whole organ culture of the postnatal sensory inner ear in simulated microgravity," *Journal of Neuroscience Methods* 171:60-71, Elsevier B.V., Amsterdam, The Netherlands (Jun. 2008).
Hiyama, E. and Hiyama, K., "Telomere and telomerase in stem cells," *British J. Cancer* 96:1020-1024, Cancer Research UK, London, UK (Mar. 2007).

Inanc, B., et al., "Osteogenic Induction of Human Periodontal Ligament Fibroblasts Under Two- and Three-Dimensional Culture Conditions," *Tissue Engineering* 12:257-266, Mary Ann Liebert, Inc., New Rochelle, NY USA (2006).
King, J.A. and Miller, W.M., "Bioreactor development for stem cell expansion and controlled differentiation," *Current Opinion in Chemical Biology* 11:394-398, Elsevier Ltd., Amsterdam, The Netherlands (Jul. 2007).
Koç, A., et al., "In Vitro Osteogenic Differentiation of Rat Mesenchymal Stem Cells in a Microgravity Bioreactor," *J. Bioactive Compatible Polymers* 23:244-261, SAGE Publications, Los Angeles, CA USA (May 2008).
Kumar, R., and Dutt, K., "Enhanced Neurotrophin Synthesis and Molecular Differentiation in Non-Transformed Human Retinal Progenitor Cells Cultured in a Rotating Bioreactor," *Tissue Engineering* 12:141-158, Mary Ann Liebert, Inc., New Rochelle, NY USA (2006).
Liu, S., et al., "Mammary stem cells, self-renewal pathways, carcinogenesis," *Breast Cancer Res.* 7:86-95, BioMed Central Ltd. (2005).
Low, H.P., et al., "Neural Precursor Cells Form Rudimentary Tissue-Like Structures in a Rotating-Wall Vessel Bioreactor," *In Vitro Cell. Dev. Biol.—Animal* 37:141-147, Society for In Vitro Biology, St. Louis, Missouri USA (2001).
Murrell, W., et al., "Multipotent Stem Cells from Adult Olfactory Mucosa," *Dev. Dynamics* 233:496-515, Wiley-Liss, Inc., NJ USA (2005).
Ohi, S., et al., "The Hematopoietic Stem Cell Therapy for Exploration of Deep Space," Space Technology and Applications International Forum, 2004, pp. 938-950; Growth of Hematopoietic Stem Cells in Space; p. 941, Purification of Culture of mHSCs in the NASA Rotating Wall Vessel, Figs. 4, 5.
Pozzobon, M., "Isolation, Expansion and Differentiation of Human Bone Marrow CD133+ Cells: Plasticity and Cardiac Regeneration," Dec. 31, 2007 (Feb. 31, 2007) Dissertation at Universita Degli Studi di Padova Dipartimento di Scienze Farmaceutiche Scuola di Dottorato di Ricera in Biologia e Medicina Della Rigenerazione.
Ratajczak, M.Z., et al., "A hypothesis for an embryonic origin of pluripotent Oct-4(+) stem cells in adult bone marrow and other tissues," *Leukemia* 21:860-867, Nature Publishing Group, England (2007).
Ribacka, C., et al., "Cancer, stem cells, and oncolytic viruses," *Ann. Med.* 40:496-505, Informa Healthcare, United Kingdom (Feb. 2008).
Russomano, T., et al., "Development and Validation of a 3D Clinostat for the Study of Cells during Microgravity Simulation," *Conf Proc IEEE Eng Med Biol Soc.* 1:564-566, IEEE Service Center, Piscataway, NJ USA (2005).
Yamaguchi, M., et al., "Serum-free coculture system for ex vivo expansion of human cord blood primitive progenitors and SCID mouse-reconstituting cells using human bone marrow primary stromal cells," *Exp. Hematol.* 29:174-182, Elsevier Science Inc., NY USA (2001).
Yuge, L., et al., "Microgravity Potentiates Stem Cell Proliferation While Sustaining the Capability of Differentiation," *Stem Cells and Development* 15:921-929, Mary Ann Liebert, Inc., Japan (2006).
Wolf, D.A, and Schwarz, R.P., "Analysis of Gravity-Induced Particle Motion and Fluid Perfusion Flow in the NASA-Designed Rotating Zero-Head-Space Tissue Culture Vessel," NASA Tech Paper 3143, Washington DC USA (1991).
Zuk, P.A., et al., "Multilineage Cells from Human Adipose Tissue: Implications for Cell-Based Therapies," *Tissue Engineering* 7:211-228, Mary Ann Liebert, Inc., CA USA (2001).
International Search Report and Written Opinion for International Application No. PCT/US09/01695, United States Patent and Trademark Office, Alexandria, Virginia, mailed on Oct. 14, 2009.
Celdyne, "Engines of Discovery," Webpage downloaded Wednesday Dec. 19, 2007, 1 page, www.celdyne.com/home/index.html.
Braccini, A., et al., "Three-Dimensional Perfusion Culture of Human Bone Marrow Cells and Generation of Osteoinductive Grafts," *Stem Cells* 23:1066-1072, Alpha Med Press, USA (2005).
Gastens, M.H., et al., "Good Manufacturing Practice-Compliant Expansion of Marrow-Derived Stem and Progenitor Cell for Cell Therapy," *Cell Transplantation* 16:685-696, Cognizant Comm. Corp., USA (2007).

(56) References Cited

OTHER PUBLICATIONS

Malda, J., and Frondoza, C.G., "Microcarriers in the engineering of cartilage and bone," Trends Biotech. 24:299-304, Elsevier Ltd., England (2006).

Randle, W.L., et al., "Integrate 3-Dimensional Expansion and Osteogenic Differentiation of Murine Embryonic Stem Cells," *Tissue Eng*. 13:2957-2970, Mary Ann Liebert, Inc., United Kingdom (2007).

Kelly, W.A., et al., "Protein Expression in *Glycine Max* Cells Under Microgravity Conditions," *Gravitational and Space Biology* 21:12, American Society for Gravitational and Space Biology, USA (2007) abstract.

Kelly, S.E., et al., "The Effects of Microgravity of Stem Cell Differentiation," *Gravitational and Space Biology* 21:18, American Society for Gravitational and Space Biology, USA (2007) abstract.

EPO, European Examination Report for corresponding European patent application No. EP 09 72 1750.9, issued Aug. 26, 2013.

Chung et al., "Human Embryonic System Cell Lines Generated without Embryo Destruction," Cell Stem Cell 2, Feb. 2006, pp. 113-117.

Bansal et al., "Tumor initiating cells," Current Pharmaceutical Biotechnology, Feb. 2009, vol. 10, No. 2, pp. 192-196.

Jones, Richard J., "Cancer stem cells clinical relevance," Journal of Molecular Medicine, Oct. 2009, vol. 87, No. 11, pp. 1105-1110.

Small et al., "Maintenance of telomeres in SV40-tranformed pre-immortal and immortal human fibroblasts," Journal of cellular Physiology, Sep. 1996, vol. 168, No. 3, pp. 727-736.

Shay et al., "Use of telomerase to create bioengineered tissues," Annals of the New York Academy of Sciences, Dec. 2005, vol. 1057, pp. 479-491.

Youn et al., "Scale-up of breast cancer stem cell aggregate cultures to suspension bioreactors," Biotechnology Progress, May 2006, vol. 22, No. 3, pp. 801-810.

Lee et al., "Tumor stem cells derived from glioblastomas cultured in bFGF amd EGF more closely mirror the phenotype and genotype of primary tumors than do serum-cultured cell lines," Cancer Cell, May 2006, vol. 9, No. 5, pp. 391-403.

Ricci-Vitiani et al., "Identification and expansion of human colon-cancer-initiating cells," Nature, Jan. 2007, vol. 445, No. 7123, pp. 111-115.

Kelly et al., "Rapid Selection and Proliferation of Cancer Stem Cells in a NASA Developed microgravity Bioreactor," Jun. 26, 2008, available at http://www.congrex.nl/08a09/Sessions/26-06?20Poster%20sessions.htm (retreived on Jun. 13, 2012.

Kelly et al., "Rapid selection and proliferation of CD133+ cells from cancer cell lines: chemotherapeutic implications," PLoS One, 2010, vol. 5, No. 4, p. E10035.

EPO, Extended Supplementary European Search Report for corresponding European patent application No. EP 09 72 1750, completed Jun. 13, 2012.

\* cited by examiner

1: Positive control
2: Negative control
3: Hos cells static growth
4: Hos cells static growth Heat Inactivated sample
5: Hos cells HFB growth – 5 days
6: Hos cells HFB growth – 5 days Heat Inactivated sample
7: Hos cells HFB growth – 10 days
8: Hos cells HFB growth – 10 days Heat Inactivated sample
9: TR8 Control 1 attomoles
10: TR8 Control 2 attomoles

METHODS FOR STEM CELL PRODUCTION AND THERAPY

CROSS REFERENCE TO RELATED APPLICATIONS

This application claims the benefit of the filing date of U.S. Provisional Patent Application No. 61/069,886, filed Mar. 18, 2008, and U.S. Provisional Patent Application No. 61/136,496, filed Sep. 9, 2008, which are each incorporated herein by reference in its entirety.

STATEMENT REGARDING FEDERALLY-SPONSORED RESEARCH AND DEVELOPMENT

Statement under MPEP 310. The U.S. government has a paid-up license in this invention and the right in limited circumstances to require the patent owner to license others on reasonable terms as provided for by the terms of NASA West Virginia Space Grant Consortium Agreement No. NNG05GF80H, awarded by the National Aeronautics and Space Administration (NASA).

Part of the work performed during development of this invention utilized U.S. Government funds. The U.S. Government has certain rights in this invention.

NAMES OF THE PARTIES TO A JOINT RESEARCH AGREEMENT

Not applicable.

BACKGROUND OF THE INVENTION

1. Field of the Invention

The present invention relates to methods for culturing stem cells in modeled microgravity conditions, including embryonic, adult, multipotent hematopoietic progenitor cells and cancer stem cells. The present invention also relates to methods for proliferating stem cells by culturing stem cells, including embryonic, adult, multipotent hematopoietic progenitor cells and cancer stem cells, under conditions of microgravity. The current invention also relates to methods for increasing telomerase activity and telomere length. Furthermore, the current invention relates to methods for culturing cancer stem cells under microgravity conditions thereby increasing their susceptibility to chemotherapeutic agents. The present invention also relates to methods for mass producing cellular factors by culturing stem cells under conditions of microgravity. Additionally, the current invention relates to a method for improving the treatment outcome of cancer in a mammal by subjecting the mammal to simulated microgravity followed by administering a chemotherapeutic agent to the mammal. The current invention also relates to a method for testing effectiveness of chemotherapy drugs on cancer stem cells.

2. Background Art

Stem cells show potential for many different areas of health and medical research. Some of the most serious medical conditions, such as cancer and birth defects, are caused by problems that occur somewhere in the process of stem cell differentiation or maintenance. Broadly, there are two different types of stem cells, embryonic stem cells and adult stem cells. Embryonic stem cells are found in blastocysts and have the ability to differentiate into all of the specialized embryonic tissues. Adult stem cells are undifferentiated cells found throughout the body after embryonic development. Adult stem cells are able to divide and replenish dying cells and regenerate damaged tissue. Furthermore, adult stem cells can maintain the normal turnover of regenerative organs such as blood, skin and intestinal tissue. Adult stem cells have the ability to divide and self-renew indefinitely and are able to generate all of the cell types of the organ from which they originate.

Stem cells can be classified as being totipotent, pluripotent, multipotent or unipotent based on their potential to differentiate into different cell types. Totipotent stem cells are produced from the fusion of gametes and the first few divisions of the fertilized egg. These cells can differentiate into embryonic and extraembryonic cell types. Pluripotent stem cells can differentiate into cells from any of the three germ layers. Multipotent calls can produce only cells of a closely related family. Unipotent cells can produce only one cell type, but have the property of self-renewal which distinguishes them from non-stem cells. Most adult stem cells are lineage restricted multipotent stem cells, and are referred to by their tissue of origin. Pluripotent adult stem cells are rare and generally small in number but can be found in a number of tissues including umbilical cord blood (Ratajczak M. Z., et al., *Leukemia* 21(5): 860-867 (2007)). There are several different types of adult stem cells including, but not limited to, adipose derived stem cells (Zuk, P. A., et al., *Tissue Engineering* 7:211-216 (2001)), epithelial stem cells, hematopoietic stem cells, mammary stem cells (Shackleton, M., et al., *Breast Cancer R E.* 7:86-95 (2005)), mesenchymal stem cells, endothelial stem cells, neural stem cells (Alvarez-Bullta, A., et al., *Brain Res. Bull.* 57:751-758 (2002)), olfactory stem cells (Murrel, W., et al., *Dev. Dyn.* 233:496-515 (2005)), testicular stem cells, dental pulp derived stem cells, and umbilical cord blood hematopoietic progenitor cells.

When an adult stem cell divides, it creates another cell like itself and a cell more differentiated than itself. This process of asymmetric cell division, gives rise to one identical daughter cell and one early transient-amplifying cell (early TA), which possesses high proliferative capacity. Through a series of cell divisions, the early TA cell gives rise to a late TA cell followed by a tissue-specific progenitor cell and finally to the bulk of differentiated cells that make up the organ or tissue (Ribacka, C., et al. *Ann. Med. epub ahead of print:* 1-10 (2008)).

Many approaches have been employed in the in vitro expansion of stem cells in the last decade, and they can be generally divided into two categories. The first category is treatment of stem cells with various combinations of stem cell expansion factors. Treatment with combinations of stem cell expansion factors has been shown to increase a progenitor/stem cell population by 2- to 30-fold in the relatively short period of 10 to 14 days. However, it is difficult to maintain stem cell activity in long-term cultures even if the total number of cells could be expanded. The second category involves using stromal cells. Several methods of in vitro expansion using primary stromal cells have been reported (Gan et al., *Blood* 90:641 (1997); Yamaguchi et al., *Exp. Hematol.* 29:174 (2001)). When stem cells were co-cultured with primary stromal cells, the stem cells were expanded for 2 to 4 weeks. It is hypothesized that stromal cells provide cell-cell or cell-extracellular matrix cues that may help expand and maintain the stem cells in an undifferentiated state. However, stem cells have frequently lost their pluripotency during in vitro expansion. Maintenance of pluripotency, number, and proliferative activity of stem cells is critical for transplantation. In addition, removal of stromal cells prior to transplantation also remains a caveat of this category.

Another type of adult stem cell is the cancer stem cell. It is known that a small percentage of cells within an established tumor have the properties of stem cells. These solid tumor stem cells give rise to both more tumor stem cells and to the majority of cells in the tumor that have lost the capacity for extensive proliferation and the ability to give rise to more tumors. Thus, solid tumor heterogeneity reflects the presence of tumor cell progeny arising from a solid tumor stem cell. Presently used means of cancer treatment would thus leave the cancer stem cells unharmed and allow them to induce regrowth of the tumor after seemingly effective treatment. Radiation therapy and most current chemotherapeutic agents target replicating cells, with adult stem cells demonstrating remarkable resistance to these treatments (Ribacka, C., et al. *Ann. Med. epub ahead of print:* 1-10 (2008)).

Thus, there is a need to establish stem cell cultures that can both expand stem cells and maintain stem cells in their undifferentiated state. In addition, there is a need for methods to increase the sensitivity of cancer stem cells to chemotherapy.

BRIEF SUMMARY OF THE INVENTION

In accordance with the present invention, it has been found that growing stem cells under certain conditions of simulated microgravity increases the life span of stem cells along with a concomitant increase in telomerase activity and telomere length. Additionally, it has been discovered by the present inventors that culturing cancer cells under certain conditions of microgravity leads to an increase in susceptibility of those cancer cells to chemotherapeutic agents.

One of the many embodiments of the present invention is directed to a method for increasing telomere length in stem cells comprising obtaining a population of stem cells, seeding the stem cells into a hydrodynamic focusing bioreactor ("HFB"), culturing said stem cells under conditions allowing for telomere growth, isolating said stem cells and determining telomere length.

An aspect of the present invention is directed to a method for increasing telomerase activity in stem cells comprising obtaining a population of stem cells, seeding the stem cells into a HFB, culturing the stem cells under conditions allowing for increased telomerase activity, isolating said stem cells and determining telomerase activity.

Another aspect of the present invention is directed to a method for increasing the life span of stem cells comprising obtaining a population of stem cells, seeding the stem cells into a HFB, culturing said stem cells under conditions allowing for increased life span, isolating the stem cells and determining telomerase activity, wherein increased telomerase activity is indicative of increased life span.

Another embodiment of the present invention is directed to a method for selectively enriching a stem cell population comprising obtaining a population of stem cells from the peripheral blood, bone marrow, umbilical cord blood and amniotic fluid, seeding the stem cells into a HFB, culturing the stem cells under conditions allowing for selective enrichment of a stem cell population, and isolating the stem cell population.

Another aspect of the present invention is directed to a method for increasing the sensitivity of cancer cells to chemotherapeutic agents comprising obtaining a population of cancer cells, seeding the cancer cells into a HFB, and culturing the cancer cells under conditions allowing for increased sensitivity of the cancer cells to chemotherapeutic agents.

Another aspect of the present invention is directed to a method for growing tissue for use in transplantation comprising growing stem cells in a HFB, allowing the stem cells to form into tissue and harvesting the tissue.

Another aspect of the present invention is directed to a method for growing tissue comprising growing cancer stem cells in a HFB, allowing the stem cells to form into cancerous tissue and harvesting the tissue.

Another aspect of the present invention is directed to a method for growing tissue for use in transplantation comprising growing cancer stem cells in a HFB, allowing the cancer stem cells to form into tissue using a scaffold or guiding matrix, killing the cancer cells in the tissue and harvesting the tissue.

Another aspect of the present invention is directed to a method for increasing telomere length in cancer stem cells comprising obtaining a population of cancer stem cells, seeding the cancer stem cells into a HFB, culturing the cancer stem cells under conditions allowing for telomere growth, isolating said stem cells and determining the telomere length.

Another aspect of the present invention is directed to a method for increasing telomerase activity in cancer stem cells comprising obtaining a population of cancer stem cells, seeding said cancer stem cells into a HFB, culturing the stem cells under conditions allowing for increase telomerase activity, isolating the stem cells and determining telomerase activity.

Another aspect of the present invention is directed to a method for increasing the life span of cancer stem cells comprising obtaining a population of stem cancer cells, seeding the stem cells into a HFB, culturing the stem cells under conditions allowing for increased life span, isolating the stem cells and determining telomerase activity, wherein increased telomerase activity is indicative of increased life span.

Another aspect of the present invention is directed to a method for producing cellular factors comprising obtaining a population of stem cells, seeding the stem cells into a HFB, culturing the stem cells under conditions allowing for production of cellular factors and harvesting said cellular factors.

Another aspect of the present invention is directed to a method for producing cellular factors comprising obtaining a population of cancer stem cells, seeding the cancer stem cells into a HFB, culturing the cancer stem cells under conditions allowing for production of cellular factors and harvesting said cellular factors.

Another aspect of the present invention is directed to a method for testing the effectiveness of chemotherapy drugs on cancer stem cells that are normally resistant to chemotherapy comprising subjecting the cancer stem cells to microgravity conditions and administering chemotherapeutic agents.

Another aspect of the present invention is directed to a method for testing the effectiveness and effects of chemotherapy drugs on normal cells comprising subjecting the normal cells to microgravity conditions and administering a chemotherapeutic agent.

Another aspect of the present invention is directed to a method for improving the treatment outcome of cancer in a mammal comprising subjecting the mammal to microgravity conditions and administering a chemotherapeutic agent.

Another aspect of the present invention is directed to a method for improving the treatment outcome of cancer that is normally resistant to chemotherapy in a mammal comprising subjecting the mammal to microgravity conditions and administering a chemotherapeutic agent.

Another aspect of the present invention is directed to a method for treating, diminishing, reducing the severity of, or eradicating cancer in a mammal comprising subjecting the mammal to microgravity conditions and administering a chemotherapeutic agent.

Another aspect of the present invention is directed to a method for treating, diminishing, reducing the severity of, or eradicating cancer that is normally resistant to chemotherapy in a mammal comprising subjecting the mammal to microgravity conditions and administering a chemotherapeutic agent.

Another aspect of the present invention is directed to a method for proliferating cells comprising seeding cancer cells into a Hydrodynamic Focusing Bioreactor and culturing said cancer cells in the presence of one or more omega-3 fatty acids.

Another aspect of the present invention is directed to a method for increasing the sensitivity of cancer cells to one or more chemotherapeutic agents comprising seeding cancer cells into a Hydrodynamic Focusing Bioreactor and culturing said cancer cells in the presence of one or more omega-3 fatty acids.

BRIEF DESCRIPTION OF THE FIGURES

The following drawings form part of the present specification and are included to further demonstrate certain aspects of the present invention. The invention may be better understood by reference to one or more of these drawings in combination with the detailed description of specific embodiments presented herein.

DETAILED DESCRIPTION OF THE INVENTION

Figure 1:
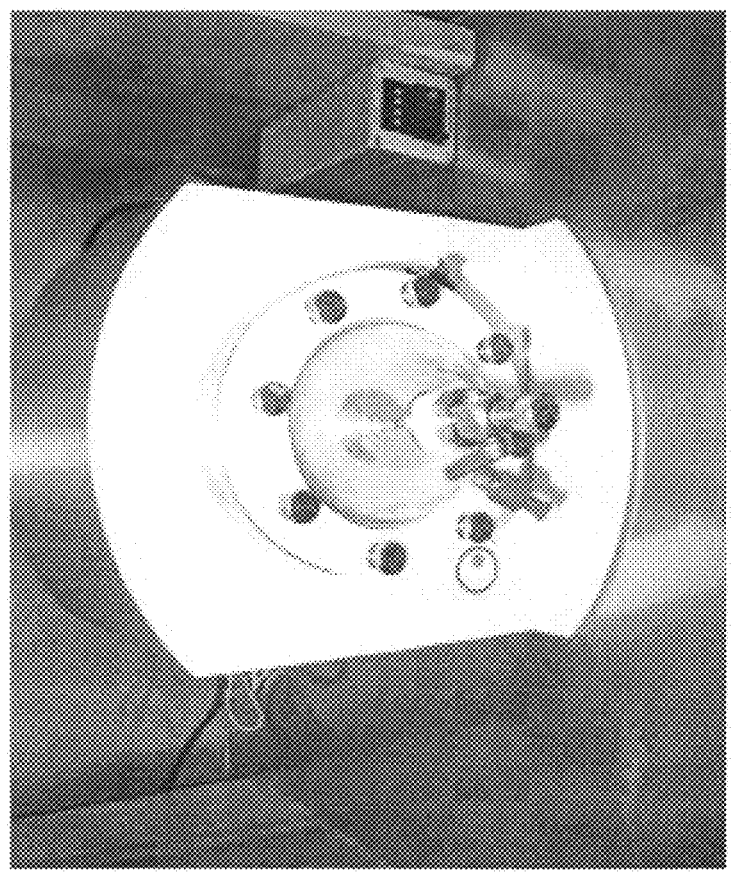
FIG. 1 shows a HFB with a 40 mL culture chamber. At the apex of the dome-shaped culture chamber is a sampling port.

The present invention offers new methods to select and proliferate stem cells using a bioreactor to eliminate gravity forces. It has been found that the bioreactor's simulation of microgravity offers a low shear environment, which promotes co-location of cells. Culture conditions in the bioreactor have also been found to provide an excellent in vitro system for increasing the telomerase activity of stem cells, thereby unexpectedly increasing telomere length and the life span of stem cells. Additionally, it has been discovered that the bioreactor's microgravity environment is also an exceptional system for increasing the susceptibility of cancer cells to chemotherapeutic agents to which they would normally be resistant.

Hydrodynamic Focusing Bioreactor (HFB)

Bioreactors have several advantages over traditional cell cultures for the mass cultivation of cells. They provide better control for scale up of cell suspension cultures under defined parameters for the production of cellular factors. Constant regulation of conditions at various stages of bioreactor operation is possible. Handling of culture such as inoculation or harvest is easy and saves time. Nutrient uptake is enhanced by submerged culture conditions which stimulate cell multiplication rate and promote higher yield of cellular factors.

It is often difficult to attain good oxygen transfer with conventional bioreactor culture. Suspension of cells is easily achievable using stirred technologies. Unfortunately, in impeller-driven bioreactors stirring invokes deleterious forces that disrupt cell aggregation and results in cell death.

Furthermore, the requirements for media oxygenation create a foaming in the bioreactor, which also tends to perturb and otherwise damage cells. These factors limit the concentration and density of the bioreactor nutrient culture medium. The conventional bioreactor approach for growing cells has the disadvantage that the mechanically stirred impellers, which damage cells, generate high shear forces and hinder proper tissue-specific differentiation.

The NASA first generation rotating bioreactors provided rotation about the horizontal axis which resulted in the suspension of cells without stirring, thus providing a suitable environment to propagate cells without sedimentation to a surface. Unfortunately, these first generation High Aspect Rotating Vessel (HARV) bioreactors did not provide a way to remove air bubbles that are disruptive to the survival of cells and the integrity of the tissue-like, three-dimensional cell constructs. When the HARV bioreactor is used, the cell growth rate is very slow compared to the general shake-flask culture method, because the lag phase is longer in order to fit the circumstance of microgravity.

Conventional bioreactors (including the Clinostat and Synthecon vessel) rely on agitation to suspend cells and attachment materials and to facilitate the mass transfer required for the growth of cells and tissue assemblies. However, shear force generated by agitation can affect cell-cell interactions and degrade three-dimensional cellular development. Moreover, air bubbles that form within the culture media in the conventional vessels cannot be removed, although such removal is critical to maintain low shear environment.

The HFB (see e.g., U.S. Pat. No. 6,001,642, which is hereby incorporated by reference in its entirety) is a horizontally rotating, fluid-filled culture vessel equipped with a membrane for diffusion gas exchange to optimize gas/oxygen-supply capable of simulating microgravity. In the HFB, at any given time, gravitational vectors are randomized and the shear stress exerted by the fluid on the synchronously moving particles is minimized. These simulated microgravity conditions facilitate spatial co-location and three-dimensional assembly of individual cells into large tissues (Wolf, D. A, and Schwartz, R. P., *Analysis of gravity-induced particle motion and fluid perfusion flow in the NASA-designed rotating zero-head-space tissue culture vessel*, NASA Tech Paper 3143, Washington D.C. (1991)).

By the term "microgravity" is meant the near weightlessness condition created inside a spacecraft as it orbits the Earth. In the simulated microgravity environment of the HFB where there is no buoyancy, no convection, no stratification of layers, and where surface tension dominates, major impacts on metabolism will be reflected in the biosynthetic potential of cultured cells and protoplasts. This is in contrast to "normal gravity" or "static conditions" by which is meant, the normal or usual gravitational force exerted on earth in a gravity-unmanipulated environment, also represented as "1G" or "1-g".

There are also significant advantages of such a system over a 1-g microenvironment found in shaker flasks. For example, cell cultures can be grown and maintained under controlled conditions with respect to nutritional and environmental requirements. Such a situation would allow establishment of conditions for optimal cell growth.

Cell culture conditions in the simulated microgravity environment of the HFB combine two beneficial factors: low shear stress, which promotes the assembly of tissue-like, three-dimensional cell constructs; and randomized gravitational vectors. Close apposition of the cells in the absence of shear forces promotes cell-cell contacts, and cell aggregation. This process then leads to the rapid establishment and expansion of tissue-like cultures, which unlike cells cultured in conventional bioreactors, are not disrupted by shear forces.

This microgravity environment of the HFB keeps cells suspended in the fluid medium without imparting shear forces that are common in conventional bioreactors. Before the introduction of the HFB, the on-orbit formation of air bubbles in culture fluid and attempts at removing these bubbles from the fluid medium of the High Aspect Rotating Vessel (HARV) bioreactor degraded both the low-shear cell culture environment and the delicate three-dimensional tissues. Unlike the HARV bioreactor, the HFB employs a variable hydrofocusing force that can control the movement, location and removal of suspended cells, three-dimensional tissues, and air bubbles from the bioreactor. Only gentle mixing is required to distribute nutrients and oxygen. These factors allow higher concentrations and densities to be achieved in a low g environment. Additionally, since the cells do not need to maintain the same surface forces that they require in Earth-normal gravity, they can divert more energy sources for growth, the biosynthesis of more products, or even novel products. This allows the ability to impose variable gravity on these cell systems and the means to test the consequences of increasing or decreasing g forces on cellular factors.

The HFB is a cell culture apparatus that employs hydrodynamic focusing to simulate microgravity. The HFB contains a rotating, cell culture chamber and an internal viscous spinner. The chamber and spinner can rotate at different speeds in either the same or opposite directions. Rotation of the chamber and viscous interaction at the spinner generate a hydrofocusing force. Adjusting the differential rotation rate between the chamber and spinner controls the magnitude of the hydrofocusing force and the co-location of contents within the culture chamber By the term "bioreactor" is meant an apparatus, such as a large chamber, for growing organisms such as bacteria, yeast, plant or mammalian cells that are used in the biotechnological production of substances such as pharmaceuticals, biopharmaceuticals, antibodies, vaccines, or for the bioconversion of organic waste.

By the term "hydrodynamic focusing bioreactor" is meant a bioreactor that relies on the principle of hydrodynamic focusing to control the movement of contents within the culture chamber of the bioreactor. By the term "hydrodynamic focusing" is meant relating to, or operated by the force of liquid in motion to control the movement of contents within the culture chamber of the bioreactor. The HFB offers a unique hydrofocusing capability that enables the creation of a low-shear culture environment simultaneously with the "herding" of suspended cells, tissue assemblies, and air bubbles.

By the term "culture chamber" is meant the enclosed space or compartment in which stem cells are cultured. In one embodiment of the present invention, the HFB is a horizontally-rotating bioreactor. In another embodiment, the bioreactor has both a culture chamber and an internal viscous spinner. The culture chamber and the internal viscous spinner can be horizontally rotated to produce a hydrofocusing force on the contents of the culture chamber. The culture chamber can also be rotated in the same direction and at the same speed as the internal viscous spinner. The culture chamber can be horizontally-rotated at a rate from about 1 RPM to about 30 RPM in 1 RPM increments. The internal viscous spinner can be horizontally-rotated from about 1 RPM to about 99 RPM, in 1 RPM increments. In a preferred embodiment, the chamber and the spinner are rotated at 25 rpm.

By the term "differential rate" is meant the difference between the rotational rate of the culture chamber and the rotational rate of the inner viscous spinner. The bioreactor can have a differential rate from about 0 RPM to about 129 RPM. Preferably, the bioreactor differential rate is from 0 to 110 RPM. More preferably, the bioreactor differential rate is between 0 and 75 RPM. In one embodiment, the chamber and the spinner are rotated in the same direction at the same speed corresponding to a differential rate of zero. This allows cells to be concentrated in front of the spinner, which has the shape of a cone.

The culture chamber can also be rotated in the opposite direction as the internal viscous spinner. The rate of rotation for the culture chamber may be higher than the rate of rotation of the internal viscous spinner, lower than the rate of rotation of the internal viscous spinner or the same as the rate of rotation of the internal viscous spinner. The bioreactor may also have a dome-shaped culture chamber.

The HFB culture chamber has a volume between about 10 mL and about 10 L. (See e.g., PCT publication WO 00/00586.) Small and medium scale laboratory cultures can be performed in culture chambers of 100 mL, 160 mL, 250 mL, and 500 mL volumes. In one embodiment, the bioreactor has a culture chamber volume of about 40 mL. Larger preparative scale cultures can be performed in culture chambers of 1 L, 5 L, and 10 L volumes. In another embodiment, the bioreactor has a culture chamber volume of 1, 2, 3, 4, 5, 6, 7, 8, 9 or 10 L. The bioreactor culture chamber can have perfusion ports to allow for gas exchange. The bioreactor culture chamber can have a sample port that allows for extraction of media, cells or air.

In one embodiment, the bioreactor allows co-location of cells with similar or differing sedimentation properties in a similar spatial region within the culture chamber. In another embodiment, the bioreactor allows freedom for the three-dimensional spatial orientation of stem cell or somatic cell tissues formed by the culturing of the stem cells. In yet another embodiment, low shear and essentially no relative motion of said culturing environment is observed with respect to the walls of the culture chamber. The resulting force within the bioreactor suspends cells in a low-shear environment such that a maximum force of about 0.01 dyne/cm$^2$ is experienced by the cell, more preferably the maximum force is about 0.001 dyne/cm$^2$. Another aspect of the invention is to a method for culturing stem cells in a HFB, whereby the resulting force within the bioreactor suspends cells in a low-shear environment such that a maximum force of about 0.5 dyne/cm$^2$ is experienced by the stem cells.

Stem Cells

There are several different types of stem cells, including embryonic stem cells, adult stem cells, and cancer stem cells. By the term "stem cells" is meant undifferentiated cells that are characterized by the ability to renew themselves through mitotic cell division and differentiation into a diverse range of specialized cell types.

Furthermore, stem cells according to the current invention may be embryonic stem cells, adult stem cells, umbilical cord blood stem cells, somatic stem cells or cancer stem cells. Additionally, the stem cells of the current invention may be hematopoietic stem cells, or mesenchymal stem cells. The stem cells of the current invention may be totipotent, pluripotent, multipotent or unipotent stem cells. Stem cells according to the current invention may be selected for by the presence of one or more stem cell markers including but not limited to: CD133, CD34, CD38, CD117/c-kit, OCT3/4, Nanog, RUNX2, SOX9, Integrin, SPARC, osteocalcin, endoglin and STRO-1. In one embodiment, the stem cells express CD133. In another embodiment, the stem cells express CD34. In yet another embodiment, the stem cells express Ki-67.

The stem cells of the current invention may be primary stem cells or may be derived from an established stem cell line, premalignant stem cell line, cancer cell line, or any cell line that manifests any stem cell marker. Primary stem cells may be derived from a cancer patient or a healthy patient.

According to the present invention, primary stem cells can be derived from a cancer patient who has any type of cancer including but not limited to a liquid tumor and a solid tumor. By the term "liquid tumor" we mean any tumor, cancer or malignancy that occurs in the fluid of a patient's body, for instance blood or lymph. By "solid organ tumor" we mean any tumor that occurs in a solid organ of a patient's body or put another way, any tumor that occurs anywhere but in the liquid of a patient's body. In particularly preferred embodiments the cancer is selected from the group consisting of leukemia, lymphoma, lung cancer, breast cancer, prostate cancer, brain cancer, pancreatic cancer, liver cancer, skin cancer and bone cancer.

Suitable cancer stem cell lines according to the current invention include but are not limited to: SAOS-2, Hos, U20S (human osteosarcoma), T98G and U87MG (human glioblastoma), Du145 and LNCap (human prostate adenosarcoma), WI38 and H23 (human lung fibroblast and lung adenosarcoma, respectively), Hep3b (human hepatocarcinoma), and HeLa (human cervical cancer), Mewo and HO-1 cells (human melanoma), HN12 and HN30 cells (human Head and Neck SquamoCellular Carcinoma).

Suitable stem cell lines according to the current invention include but are not limited to the following cell lines (NIH Code): BG01, BG02, BG04, SA01, SA02, SA03, ES01, ES02, ES03, ES04, ES05, ES06, TE03, TE32, TE33, TE04, TE06, TE62, TE07, TE72, UC01, UC06, WA01, WA07, WA09, WA13, WA14. The stem cells according to the present invention may also be modified stem cells. The modified stem cells may be genetically modified to increase production of a cellular factor(s) including growth factors, cytokines, differentiation factors, and hormones.

A stem cell population of the present invention may also be selectively enriched by obtaining a population of stem cells, seeding the stem cells into a HFB, culturing the stem cells under conditions allowing for selective enrichment of a stem cell population, and isolating the stem cell population. Preferred conditions include loading the bioreactor with an enriched stem cell population preselected by MACSorting or loading a heterogenous population from which the stem cells can be selected by the microgravity environment. A population of stem cells is selectively enriched by the following procedure: the microgravity environment of the bioreactor provides a mechanism for selecting stem cells by apoptosis of the differentiated cells present in the heterogenous population.

Telomeres and Telomerase

The present inventors have discovered that stem cells grown under conditions of simulated microgravity show enhanced telomerase activity and thus an increase in telomere length. The telomere is a functional complex consisting of tandem guanine rich repeated DNA and its associated proteins located at the ends of each linear chromosome (Cong, U. and Shay, J. W., *Cell Res.* 18:725-732 (2008)). In human chromosomes, telomeres consist of thousands of copies of 6 base repeats (TTAGGG). The function of the telomere is to protect chromosomes from end to end fusions, recombination, and terminal DNA degradation. The length of the short guanine-rich repeat sequences is heterogeneous among individuals ranging between 5 and 20 Kb according to age, organ and the proliferate history of each cell (Hiyama E. and Hiyama, K., *British J. Cancer* 96:1020-1024 (2007)). During DNA synthesis and cell division, telomeres shorten as a result of incomplete replication of linear chromosomes. This progressive telomere shortening is one of the molecular mechanisms underlying ageing, as critically short telomeres trigger chromosome senescence and loss of cell viability. Id.

Telomeres can be lengthened, however, by a complex of a reverse transcriptase protein encoded by the TERT gene and a template RNA TERC, which together form the enzyme telomerase. Telomerase can add telomeric repeats onto the chromosome ends and prevent the replication dependent loss of telomere and cellular senescence. Therefore, telomerase activity and telomere length maintenance are associated with the immortality of cancer cells, germ line cells and embryonic stem cells.

Thus, an aspect of the present invention is directed to a method for increasing the length of telomeres in stem cells by obtaining a population of stem cells, seeding said stem cells into a HFB, culturing said stem cells under conditions allowing for telomere growth and determining the telomere length. By "conditions allowing for telomere growth" is meant any culture condition which leads to an increase in telomere growth in the stem cell. A preferred culture condition is growing the cells in microgravity environment for 1 to 15 days as in Example 8. Telomere length can be indirectly measured by methods known in the art such as the telomeric repeat amplification protocol (TRAP) assay. The quantification of telomerase activity can be measured by TRAP assay. The methods of the current invention lead to an increase in telomere length of 6 to 24 repeats when compared to stem cell cultures grown under static conditions.

Another aspect of the present invention is directed to a method for increasing telomerase activity in stem cells by obtaining a population of stem cells, seeding said stem cells into a HFB, culturing said stem cells under conditions allowing for an increase in telomerase activity and assaying for telomerase activity. By "conditions allowing for an increase in telomerase activity" is meant any culture condition which leads to an increase in telomerase activity in the stem cell. A preferred culture condition is exposing the cells to the microgravity environment from 1 to 15 days, including, but not limited to the combination of either commonly used media for cell culture such as RPMI-1640, E-MEM, D-MEM, in the presence or absence of fetal bovine serum (FBS), calf serum (CS), or specially designed media for stem cell culture including growth factors. An increase in telomerase activity can be measured by methods known in the art such as TRAP assay, TRAP enzyme linked immuno-sorbant assay (TRAP ELISA), transcription mediated amplification (TMA), and analysis of the hTERT transcript. The methods of the current invention lead to a 1 to 5 fold increase in telomease activity when compared to stem cells grown in static conditions.

Another aspect of the present invention is directed to a method of increasing the life span in stem cells by obtaining a population of stem cells, seeding said stem cells into an HFB, culturing said stem cells under conditions allowing for an increase in life span and assaying for increased telomerase activity, wherein an increase in telomerase activity is indicative of increased life span. By "conditions allowing for an increase in life span," is meant any culture condition which leads to an increase in life span of the stem cell. A preferred culture condition is exposing the cells to the microgravity environment from 1 to 15 days, including but not limited to the combination of either commonly used media for cell culture such as RPMI-1640, E-MEM, D-MEM, in the presence or absence of FBS or CS, or specially designed media for stem cell culture including growth factors.

Growth Conditions

Growth conditions according to the present invention are any conditions that allow for growth of the cultured stem cells. It is contemplated that the media within the culture chamber of the bioreactor can be oxygenated. It is also contemplated that the byproducts formed within the culture chamber of the bioreactor can be removed. These byproducts can be removed through the sampling port of the HFB. By the term "byproducts" is meant substances left over from stem cell culture. In one embodiment, air bubbles formed within the culture chamber of the bioreactor can be removed. Air bubbles can be removed through the sampling port of the HFB.

Media is exchanged from the bioreactor vessel for a variety of reasons, including to induce protein, lipid, nucleic acid, metabolite or chemical production, byproducts, or to restart growth of the cells after nutrient depletion. One of skill in the art will understand that media exchange can be carried out in a variety of ways. Sterile media can be added after filtration through a sterile filter. Fresh medium can be added to the cells. The fresh medium may have the same components or different components than the original unspent medium. For example, "induction medium" may be exchanged with "growth medium," or the reverse may also occur. By the term "induction medium" is meant culture medium which provides a culture environment that activates transcription or alleviates repression of transcription from an inducible promoter. By the term "inducing agent" is meant byproducts present in conditioned media that allow for the enhanced production of a cellular factor of interest.

When cells proliferate, the pH of the medium lowers as catabolites are released in the medium. The methods further include adjusting the pH of the fluid culture medium. In one embodiment, the upper pH limit for medium exchange will be about pH 7.4. One of skill in the art will recognize that the pH value for optimal cell growth, protein, metabolite or chemical production will vary with the culture conditions, the type of cells, and the cellular factor being produced. Measurement of pH is well known to those of skill in the art. The pH can be measured using a pH electrode in combination with a device for reporting the pH. The pH can also be detected using pH sensitive dyes, usually bound to a paper support. The pH electrodes, pH meters, and pH paper are all commercially available from, for example, Fisher Scientific, Inc., and Broadley-James Corporation. The bioreactor will preferably include means to measure pH levels in the culture media. Change in pH can be monitored, not measured, by presence in the medium of pH sensitive dyes such as phenol-red. The media containing the pH sensitive dye are commercially available from, for example, Fisher Scientific, Inc. and CellGrow.

Cells are grown under sterile conditions with controlled dissolved $O_2$ levels. One of skill in the art would know how to measure dissolved oxygen levels in media, and how to use those levels to determine the rate of oxygen consumption over time. Dissolved oxygen sensors are commercially available from, for example, Broadley-James Corporation and Mettler Toledo Corporation. In one embodiment, the method includes adjusting the dissolved oxygen levels of the culture medium. In a particular embodiment, the dissolved oxygen levels in the culture medium can be elevated by using a bubble-trap oxygenator. In another embodiment, the method includes adjusting the oxygen levels of the culture incubator in which the bioreactor culture chamber is rotating. The bioreactor will preferably include means to measure dissolved $O_2$ levels. Measurements can be taken online, within the bioreactor culture chamber or measurements can be taken offline, after samples of the medium have been withdrawn from the culture chamber, however, online measurements are preferred. These operations are included with HFB bioreactors commercially available from, for example, Celdyne Corp.

The stem cells of the current invention are preferably cultured at a temperature of about 35° to about 39° C., more preferably at a temperature of about 37° C.

Additionally, the stem cells of the current invention are preferably cultured in the HFB for about 1 to about 35 days, about 1 to about 25 days, about 1 to about 15 days, about 3 to about 7 days, or for about 3, 5 or 7 days.

The stem cells of the current invention are cultured at an initial concentration of about 0.5 to about $2.5 \times 10^3$ cells/mL of medium, or even up to $5 \times 10^4$ cells/mL of medium or up to $1 \times 10^6$ cells/mL of medium, more preferably at a concentration of about $2.5 \times 10^5$ cells/mL medium or $0.5 \times 10^6$ cells/mL medium.

In addition, the rotational speed of the HFB in accordance with the present invention is from about 1 to about 30 rpm, more preferably about 25 rpm.

Additionally, the stem cells according to the current invention are cultured in a culture medium comprising from about 0 to about 20 percent serum, preferably from about 0 to about 10 percent, most preferably 10 percent. The serum can be from any usual source for use in cell culture. In a preferred embodiment, the serum is fetal bovine serum.

In addition, the culture medium may also contain antibiotics and/or antifungals. Any antibiotic or antifungal for use in cell culture may be used, such as penicillin, streptomycin, gentamycin, hygromycin, kanamycin, neomycin, puromycin and tetracycline. The antibiotics can be present in amounts that are non-toxic to the cell culture of between 1 unit/mL and 100 units/mL, or between 1 μg/mL and 100 μg/mL.

The culture medium may also contain amino acids or mixtures of essential and/or non-essential amino acids. The amino acids can be present in an amount of between 1 unit/mL and 100 units/mL, or between 1 µg/mL and 100 µg/mL.

The medium may also contain stem cell growth factors. Examples of stem cell growth factors suitable in accordance with the present invention include but are not limited to: Flk-2/Flt-3 ligand (FL), stem cell factor (SCF), thrombopoietin (TPO), granulocyte-colony stimulating factor (G-CSF), megakaryocyte growth and development factor (MGDF), interleukin-3 (IL-3), and IL-6.

The culture medium may also contain one or more omega-3 fatty acids. Omega-3 fatty acids that can be used in various aspects of the present invention include α-linolenic acid, eicosapentaenoic acid (EPA), docosahexaenoic acid (DHA), stearidonic acid (STD), eicosatrienoic acid (ETE), eicosatetraenoic acid, docosapentaenoic acid (DPA), tetracosapentaenoic acid, tetracosahexaenoic acid (nisinic acid), and combinations thereof. The use of other omega-3 fatty acids known in the art is also contemplated. The omega-3 fatty acids can be used in concentrations between about 0.1 µM and about 100 µM. More preferably, they can be used in concentrations of between about 1 nM and about 100 µM, between about 1 µM and 100 µM, between about 10 µM and about 100 µM, between about 20 µM and about 80 µM, between about 30 µM and about 70 µM and between about 50 µM and about 60 µM. Most preferably, they are used in concentrations of about 25 µM, about 50 µM or about 75 µM.

Chemotherapeutic Agents

Chemotherapy, or the use of chemotherapeutic agents, to destroy cancer cells is a mainstay in the treatment of malignancies. By the term "chemotherapeutic agents" is meant any pharmacological agent that is of use in the treatment of cancer. Most chemotherapeutic agents kill cancer cells by affecting DNA synthesis. Examples of classes of chemotherapeutic agents include alkylating agents, inhibitors of topoisomerase II, cytoskeletal disrupters, nucleoside analogs, platinum based agents, retinoids, anthracyclines, nitrosoureas, antimetabolites, antitumor antibiotics, vinca alkaloids, and steroid hormones. Specifically, chemotherapeutic agents of the current invention include one or more of cyclophosphamide, mechlorethamine, chlorambucil, melphalan, daunorubicin, doxorubicin, epirubicin, idarubicin, mitoxantrone, valrubicin, paclitaxel, docetaxel, etoposide, teniposide, tafluposide, azacitidine, azathrioprine, cytarabien, doxifluridine, fluourouracil, gemcitabine, meracaptopurine, methotrexate, tioguanine, bleomycin, carboplatin, cisplatin, oxaliplatin, all-trans retinoic acid, vinblastine, vincristine, vindesine, and vinorelbine. Most preferably, chemotherapeutic agents of the current invention include cisplatin, doxorubicin and methotrexate.

Chemotherapeutic amounts for in vivo chemotherapy are well known. For example, amounts that can be added to cell cultures are from about 1 to about 20 µg/mL of cisplatin, from about 5 to about 15 µg/mL, about 5, about 10, or about 15 µg/mL cisplatin; about 1 to about 50 µg/mL of methotrexate, from about 4 to about 45 µg/mL, most preferably about 4, 11, 22, or about 45 µg/mL methotrexate; or from about 0.25 to about 5 µg/mL of doxorubicin, from about 0.5 to about 2.5 µg/mL, or about 0.5, 1.1, or about 2.5 µg/mL doxorubicin may be used in accordance with the invention.

Chemotherapeutic agents may be administered to a mammal, such as a human patient, in need thereof by any means of administration including oral, intravenous, subcutaneous, transdermal, transmucosal, intramuscularly or intraperitoneally. One of ordinary skill in the art would recognize in what manner and at what dose a specific type of chemotherapeutic agent in a specific mammal should be used.

Cellular Factors

Many types of cellular factors can be mass-produced using the present invention. By the term "cellular factor" is meant a substance that is produced by a cell. The cellular factors being produced include: proteins, lipids, nucleic acids, metabolites, biochemicals, and byproducts. Some of the proteins of interest include without limitation, growth factors, differentiation factors, cytokines, therapeutic proteins, antibodies, enzymes, protease inhibitors, transport proteins, storage proteins, protein toxins, hormones, and structural proteins. Since cells are retained in the chamber culture during continuous culture, the cellular factor is preferably secreted into the medium. Cellular factors may be native to the stem cell or encoded by genes "endogenous" to the stem cell. For example, stem cells of the bone will express bone morphogenic proteins (BMPs). Other examples of cellular factors include, transcription factors, kineases, kinase inhibitors, cyclins, tumor suppressor genes, oncogenes, transmembrane proteins, receptors, secreted proteins, enzymes, protoenzymes, diffusible proteins, secreted proteins, antiangiogenic proteins, proangiogenic proteins, intracellular proteins, cytoplasmic proteins, nuclear proteins, RNA trafficking proteins, DNA trafficking proteins, ion trafficking proteins, chaperones, ubiquitones, sumolating proteins, differentiating proteins, chondrogenic proteins, interleukins, and any other factors or cellular products synthesized by a mammalian cell.

Alternatively, cellular factors may be expressed from transgenic stem cells. Transgenic stem cells may carry an "exogenous" gene that encodes a protein of interest. Proteins expressed from exogenous genes may be engineered to include a signal peptide for secretion, if the protein is not normally secreted.

The presence of cellular factors made by stem cells can be assayed. Stem cells that are secreted into the media can be collected with media through the sampling port. Cellular factors that are retained in stem cells can be collected in cell culture samples through the sampling port. In one embodiment of the present invention, the cellular factors being assayed are selected from the group consisting of: proteins, lipids, nucleic acids, metabolites, biochemicals, and byproducts. Cellular factors in stem cells obtained with media, as well as cellular factors obtained by harvesting cell culture samples, can be purified and concentrated by methods known to those of skill in the art. In one embodiment, the presence of cellular factors can be determined by purifying the cellular factors from cell lysates or other complex mixtures through reverse-phase HPLC, capillary electrophoresis, ion exchange, or size exclusion chromatography.

In another embodiment, the cellular factor is a protein. In one embodiment, the protein can be assayed by its level of expression. In another embodiment, the protein can be assayed by determining its catalytic activity. In another embodiment, the protein can be assayed by determining its ability to bind to other proteins and small molecules by measuring its dissociation constant ($K_d$). By the term "dissociation constant" is meant the equilibrium constant for a reversible dissociation reaction. By the term "equilibrium constant" is meant the ratio of concentrations of reactants and products when equilibrium is reached in a reversible reaction. By the term "equilibrium" is meant the state at which rate of the forward chemical reaction equals the rate of the reverse chemical reaction.

When the cellular factor is a protein from a transgenic stem cell, DNA transgenes may be introduced into the genome of the stem cell host by a variety of conventional techniques. For example, the DNA constructs may be introduced directly into the genomic DNA of the stem cell using techniques such as electroporation and microinjection of stem cell cytoplasm, or the DNA constructs can be introduced directly to stem cells using ballistic methods, such as DNA particle bombardment. Other ways of introducing transgenes is with the use of viral particles such as retroviruses or adenoviruses that will transfer the RNA or DNA construct into the target cell.

If an appropriate antibody is available, immunoassays can be used to qualitatively or quantitatively analyze the cellular factor produced by the present invention. A general overview of the applicable technology can be found in Harlow & Lane, *Antibodies: A Laboratory Manual* (1988).

The proteins of interest can be detected and/or quantified using any of a number of well-recognized immunological binding assays (see, e.g., U.S. Pat. Nos. 4,366,241; 4,376, 110; 4,517,288; and 4,837,168). For a review of general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to an antigen of choice. The antibody may be produced by any of a number of means well known to those of skill in the art and as described in Harlow & Lane, *Antibodies: A Laboratory Manual* (1988).

Western blot (immunoblot) analysis may be used to detect and quantify the presence of a protein of interest in the sample. Western blot analysis can further be used to ensure a full-length protein has been produced. The technique generally comprises separating sample proteins by gel electrophoresis on the basis of molecular weight, transferring the separated proteins to a suitable solid support, (such as a nitrocellulose filter, a nylon filter, or derived nylon filter), and incubating the sample with the antibodies that specifically bind the protein of interest. The antibodies may be directly labeled or alternatively may be subsequently detected using labeled secondary antibodies (e.g., labeled sheep anti-mouse antibodies) that specifically bind to the primary antibodies.

Many different cellular factors can be expressed using the present invention; thus, many different assays for functional compounds may be employed. One of skill in the art will be aware of the particular assay most appropriate to determine the functional activity of the expressed cellular factors.

Therapeutic Uses

The inventors have discovered that culturing stem cells under microgravity conditions is useful for several applications. For example, stem cells grown under microgravity conditions form three-dimensional tissues for transplantation. Examples of tissues that can be grown for transplant include, bone, teeth, skin, cartilage, an internal organ, tissue derived from hair follicles, liver, pancreas, cornea, kidney, heart, muscle or brain. Additionally, cancer stem cells grown under microgravity conditions display increased sensitivity to chemotherapeutic agents, which is useful in the treatment of cancer. In addition, a mammal with cancer can be subjected to simulated microgravity conditions in accordance with the present invention to increase the sensitivity of the cancer stem cells of the mammal to chemotherapeutic agents, thereby improving the treatment outcome of cancer in the mammal.

All references cited in the Examples are incorporated herein by reference in their entireties.

EXAMPLES

Example 1

Operation of the HFB

The HFB is an enabling technology for three-dimensional cell culture and tissue engineering investigations both in laboratories on Earth and on orbiting spacecraft. The HFB used in establishing SAOS-2 cell suspension cultures contains a rotating, dome-shaped cell culture chamber with a centrally located sampling port and an internal viscous spinner (see FIG. 1). The chamber and spinner can rotate at different speeds in either the same or opposite directions. Rotation of the chamber and viscous interaction at the spinner generate a hydrofocusing force. Adjusting the differential rotation rate between the chamber and spinner controls the magnitude of the force. The HFB is equipped with a membrane for diffusion gas exchange to optimize gas/oxygen supply. Under the microgravity conditions of the HFB, at any given time, gravitational vectors are randomized and the shear stress exerted by the fluid on the synchronously moving particles is minimized. These simulated microgravity conditions facilitate spatial co-location and three-dimensional assembly of individual cells into large tissues (See e.g., Wolf, D. A. and Schwartz, R. P., *Analysis of gravity-induced particle motion and fluid perfusion flow in the NASA-designed rotating zero-head-space tissue culture vessel.*, Washington D.C., NASA Tech Paper 3134, (1991).) In promoting three-dimensional tissue culture, an average shear value of 0.001 dynes/cm$^2$ was estimated for a rotation rate of 10 RPM. (See, e.g., Gonda, S. R. and Spaulding, G. F., Hydrofocusing Bioreactor for Three-Dimensional Cell Culture, NASA Tech Brief MSC-22538, Washington D.C. (2003).)

The HFB model used to establish SAOS-2 cell suspension cultures is the HFB-40 mL, Celdyne, Inc., Houston, Tex. This model is supplied with a 40 mL culture chamber and a differential spinner drive to facilitate the positional control of cells and tissues within the chamber. The chamber rotation rate can be set with crystal-controlled accuracy from 1 to 30 RPM in 1 RPM increments. The HFB is operated inside of a Laminar Flow Hood. Aspetic techniques are employed when adding culture medium or innoculum to the culture chamber. After culture medium or innoculum medium addition, air bubbles are extracted via the sampling port to ensure that the HFB culture chamber is air-tight.

Example 2

Selection of Cancer Cells in the HFB

Figure 2:
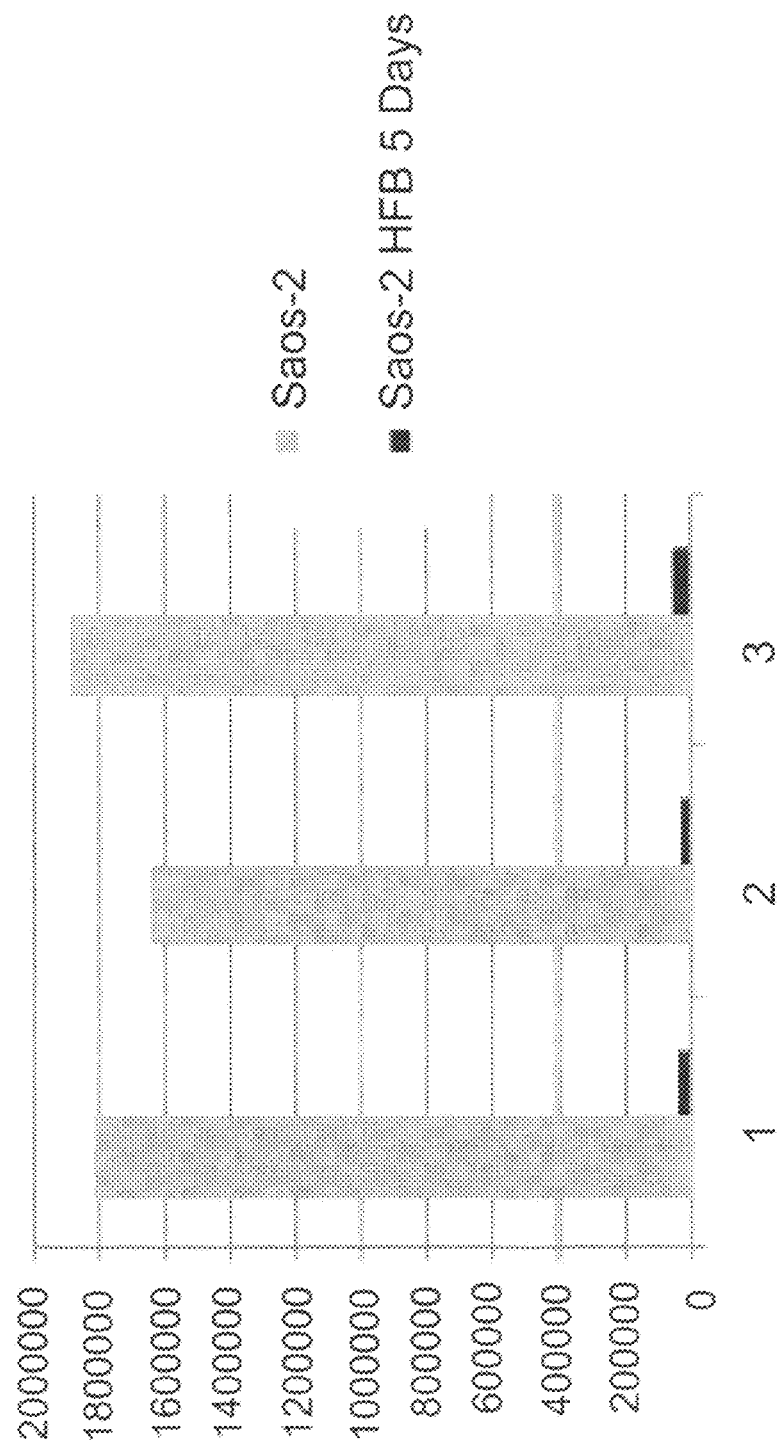
FIG. 2 shows the number of viable cells recovered after culture of SAOS-2 osteosarcoma cells in HFB for 5 days.

SAOS-2 osteosarcoma cells were seeded into a HFB at concentrations ranging between about $2.5 \times 10^3$ cells/mL to $5 \times 10^4$ cells/mL medium. The rotational speed of the HFB was 25 rpm and the microgravitational force exerted by the HFB was 0.0174 g. The cells were grown in an incubator under these conditions: D-MEM medium containing 10% FBS, 1 mM L-Glutamine, 100 U/mL Penicillin, and 100 µg/mL of Streptomycin was used at 37° C. and with 5% $CO_2$ for 5 days. After 5 days, the cells were assayed for viability by trypan blue exclusion cell count. The results show that compared to control cells, SAOS-2 cells grown in the HFB showed significantly lower viability (see FIG. 2)

Example 3

Sorted CD133$^+$ Stem Cells Derived from SAOS-2 Cells Proliferate in HFB

Figure 3:
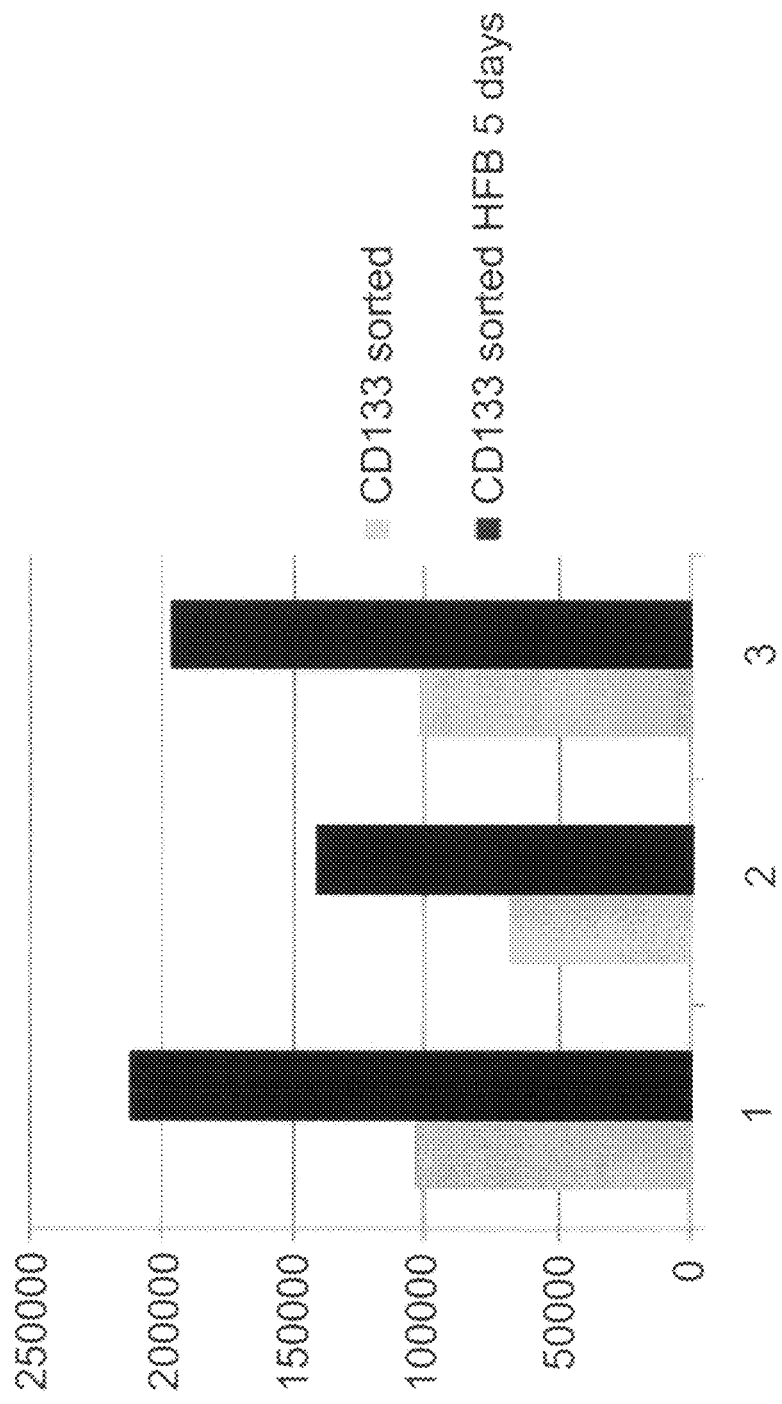
FIG. 3 shows the number of viable cells MACSorted with an antibody to CD133 and cultured in the HFB for 5 days.

SAOS-2 cells were MACSorted with an antibody against CD133 conjugated to magnetic beads. The sorted CD133 positive cells were grown in the HFB as in Example 2. After 5 days, cells were assayed for viability by trypan blue exclusion cell count. In three separate experiments, after 5 days, sorted CD133$^+$ cells had expanded significantly, by approximately 2-3 fold (see FIG. 3). CD133 positive MACSorted SAOS-2 osteosarcoma cells were seeded into a HFB at a concentration of about $2 \times 10^4$ cells/mL medium. The rotational speed of the HFB was 25 rpm and the microgravitational force exerted by the HFB was 0.0174 g. The cells were grown in an incubator under these conditions: D-MEM medium containing 10% FBS, 1 mM L-Glutamine, 100 U/mL penicillin, and 100 µg/mL of Streptomycin was used at 37° C. and with 5% $CO_2$ for 5 days. After 5 days, the cells were assayed for viability by trypan blue exclusion cell count.

Example 4

Figure 4:
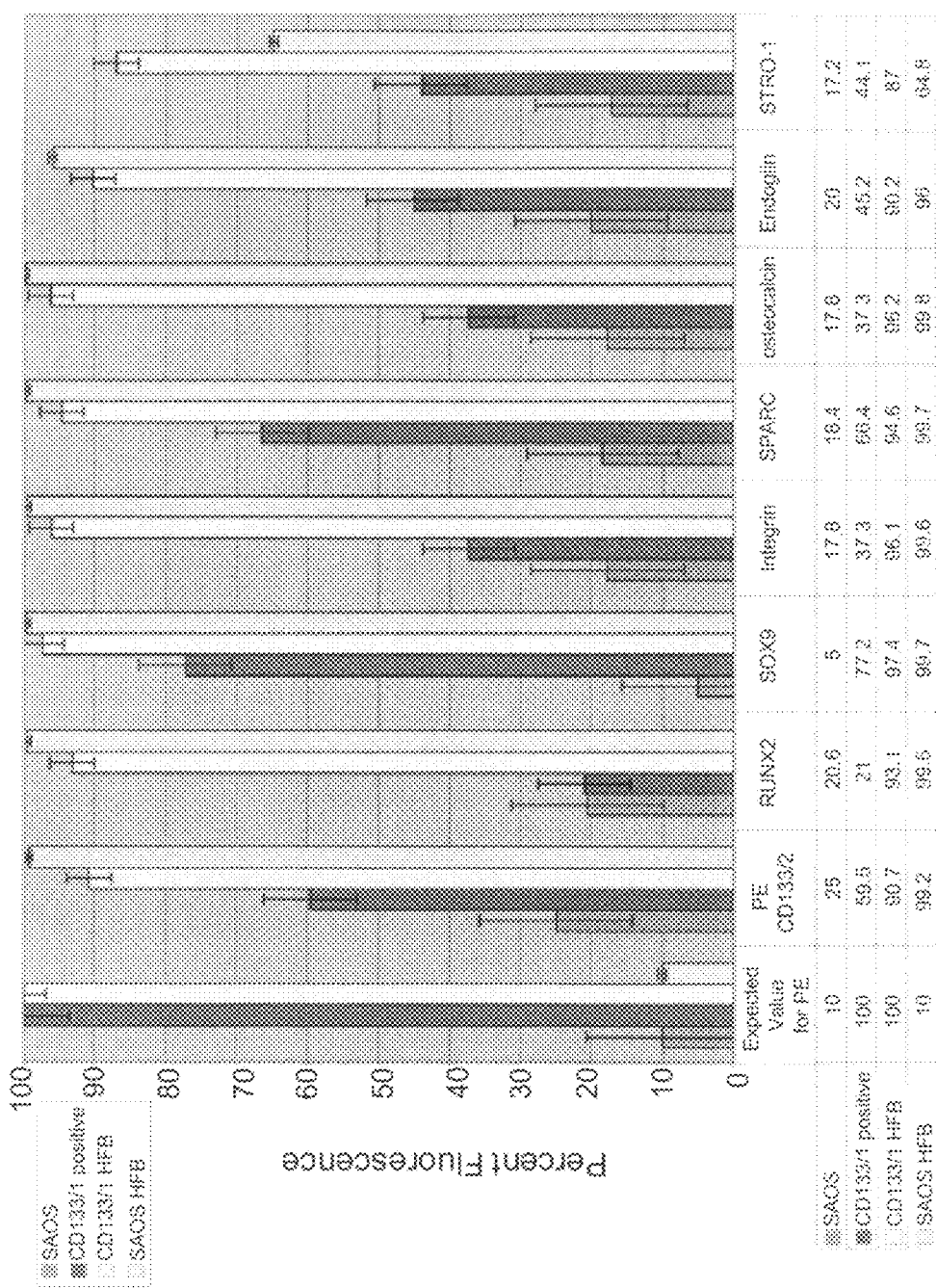
FIG. 4 shows other stem cell markers expressed on SAOS-2 osteosarcoma cells, CD133 positive SAOS-2 cells, sorted CD133 positive SAOS-2 cells cultured in the HFB, and unsorted SAOS-2 cells grown in the HFB.

Optimization of Proliferation in HFB of Sorted CD133$^+$ Stem Cells Derived from SAOS-2 Cells SAOS-2 cells were MACSorted with an antibody against CD133 conjugated to magnetic beads. The sorted CD133 positive cells were grown in the HFB as in Example 2. After 7 days, cells were assayed for viability by trypan blue exclusion cell count. In three separate experiments, after 7 days, sorted CD133$^+$ cells had expanded significantly, by approximately 15 fold (see FIG. 4). CD133 positive MACSorted SAOS-2 osteosarcoma cells were seeded into a HFB at a concentration of about $5 \times 10^2$ cells/mL medium. The rotational speed of the HFB was 25 rpm and the microgravitational form exerted by the HFB was 0.0174 g. The cells were grown in an incubator under these conditions: D-MEM containing 10% FBS, 1 mM L-Glutamine, 100 U/mL penicillin, and 100 µg/mL of streptomycin was used at 37° C. and with 5% $CO_2$ for 7 days. We achieved a 15-fold proliferation of CD133$^+$ cancer stem-like cells from the parental SAOS-2 cells over a seven-day period by stopping the reactor every 24 hours and gently mixing the culture 10 times in an orthogonal manner over a period of one minute, which allowed for redistribution of the media in the dome and mixing of the nutrient with the proliferating cells.

Example 5

Figure 5:
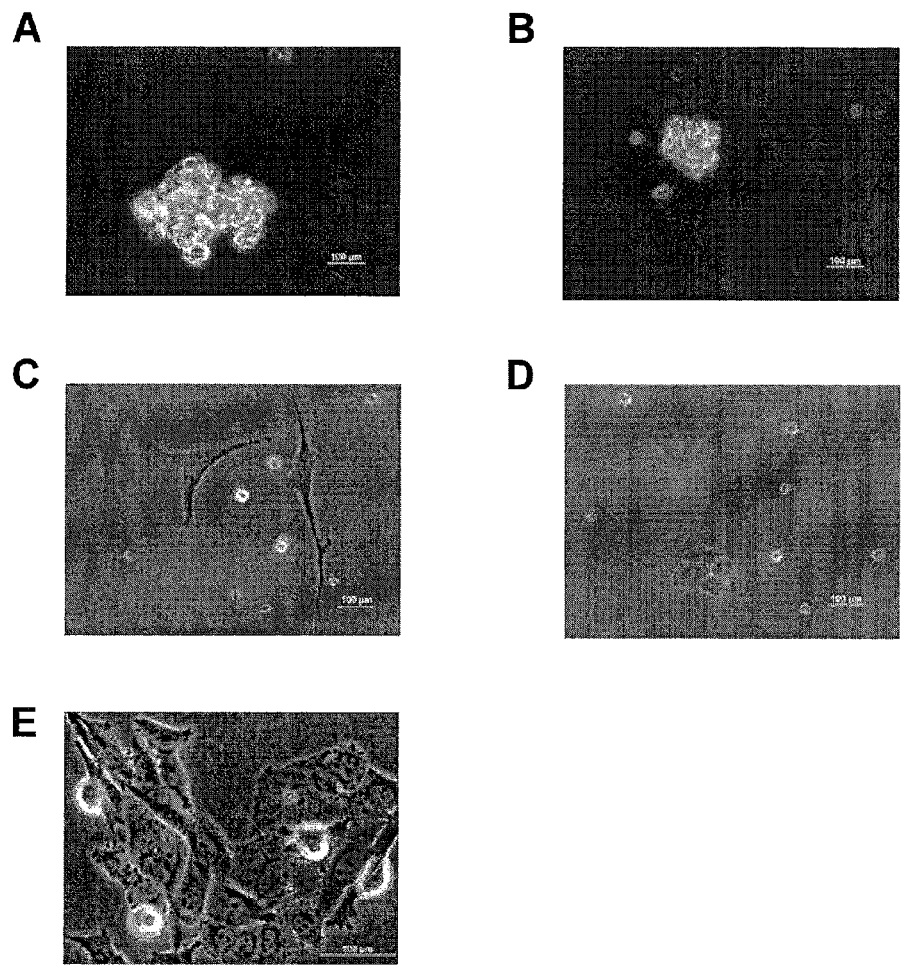
FIG. 5 is a bright field image of cellular cluster formation of sorted CD133 positive SAOS-2 osteosarcoma cells grown in the bioreactor for 3 days (5A, 5B, 5C) or in adhering tissue culture dishes for 3 days (5D, 5E).

SAOS-2 Cells Cultured in the HFB Display Increased Expression of Stem Cell Markers To further characterize these cells, sorted CD133$^+$ SAOS-2 cells grown for 5 days in static culture, sorted CD133$^+$ SAOS-2 cells grown for 5 days in the HFB, unsorted SAOS-2 cells grown in static culture, and unsorted SAOS-2 cells grown in HFB were assayed for the presence of other stem cell markers (RUNX2, SOX9, Integrin, SPARC, osteocalcin, Endoglin, and STRO-1). The results show that for all stem cell markers, SAOS-2 cells, CD133$^+$ sorted or unsorted, grown in HFB expressed significantly higher levels of the markers (see FIG. 5). Specifically, the level of expression of these stem cell markers increased between about 20% and about 80% in CD133$^+$ cells grown in the HFB compared to CD133$^+$ cells grown under conditions of normal gravity. SAOS-2 osteosarcoma cells were seeded into a HFB at a concentration of about $6 \times 10^4$ cells/mL medium. The rotational speed of the HFB was 25 rpm and the microgravitational force exerted by the HFB was 0.0174 g. The cells were grown in an incubator under these conditions: D-MEM medium containing 10% FBS, 1 mM L-Glutamine, 100 U/mL Penicillin, and 100 µg/mL of streptomycin was used at 37° C. and with 5% $CO_2$ for 5 days. After 5 days, the cells were stained with the described antibodies and processed by flow cytometry for expression of the selected markers.

Example 6

Figure 6:
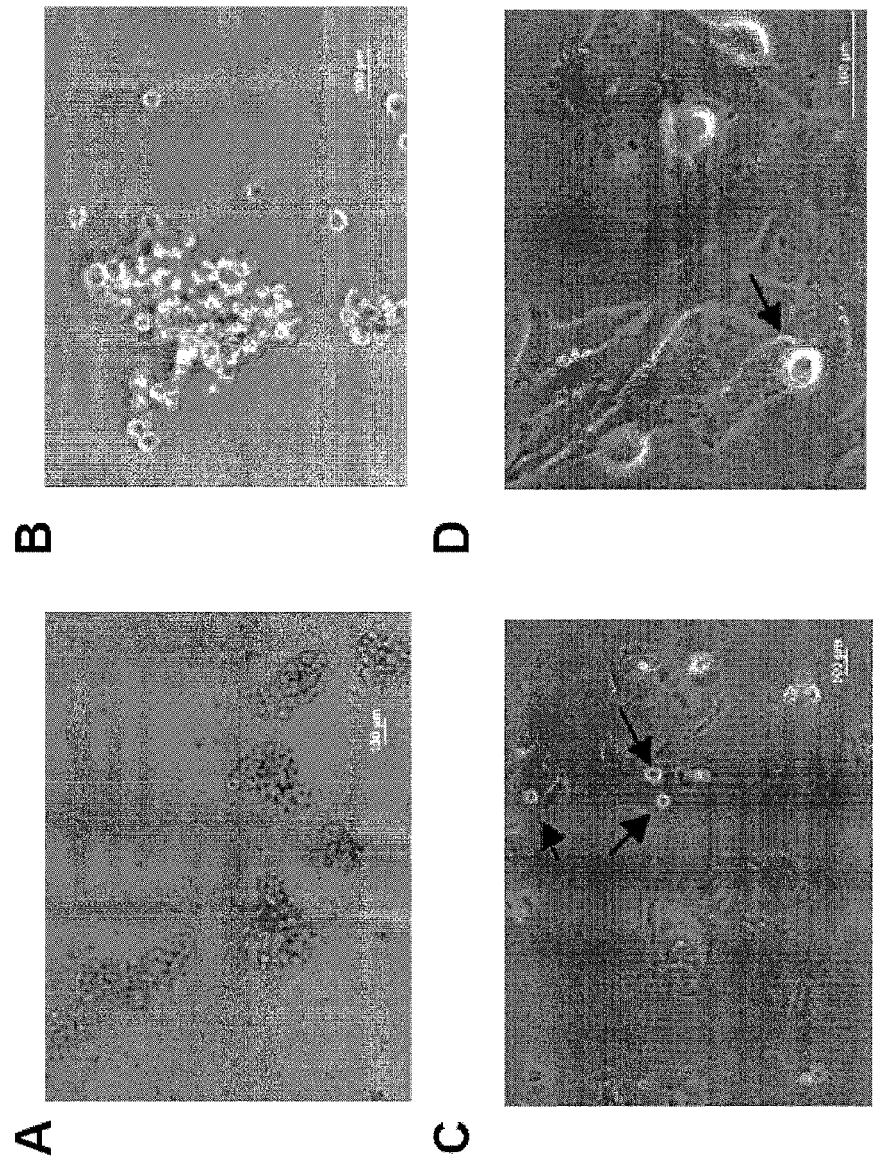
FIG. 6 shows cell clusters formed by SAOS-2 CD133 positive sorted cells in non-adhering dishes (6A and 6B); adherent and differentiated SAOS-2 cells derived from a SAOS-2 CD133 positive cells grown in adherent culture dishes (6C and 6D); and a SAOS-2 cell line reconstituted after one week of inoculation of CD133 positive enriched cells in adhering tissue culture dishes.

CD133$^+$ Enriched Osteosarcoma Cells Proliferate and Assemble into Three-Dimensional Sarcospheres in the HFB CD133$^+$ enriched SAOS-2 osteosarcoma cells were seeded into a HFB at a concentration of $2.5 \times 10^5$ cells/mL medium. The rotational speed of the HFB was 25 rpm and the microgravitational force exerted by the HFB was 0.0174 g. The cells were grown in an incubator under these conditions: D-MEM medium containing 10% FBS, 1 mM L-Glutamine, 100 U/mL Penicillin, and 100 µg/mL of streptomycin was used at 37° C. and with 5% $CO_2$ for 3 days. After 3 days, the cells were visualized by microscopy at a magnification of 10× and 40× (FIGS. 6A and 6B, respectively) for the presence of three-dimensional sarcospheres. The results show that CD133$^+$ SAOS-2 cells are able to proliferate in the HFB and assemble three-dimensionally as sarcospheres (FIG. 6).

CD133$^+$ sorted SAOS-2 cells enriched from growth in HFB for 3-5 days under the conditions described in Example 2 were also tested for their ability to attach to culture dishes and reconstitute the parent SAOS-2 cell line, by placing CD133$^+$ sorted SAOS-2 cells grown in HFB (FIGS. 6A and 6B) back into adherent cultures (FIGS. 6C and 6D) and visualizing the cells for differentiation at 10× and 40×, respectively.

The results show that CD133$^+$ sorted SAOS-2 cells grown in HFB are able to reconstitute the parent SAOS-2 line in adherent dishes after one week in culture in an incubator under these conditions: D-MEM medium containing 10% FBS, 1 mM L-Glutamine, 100 U/mL Penicillin, and 100 µg/mL of streptomycin was used at 37° C. and with 5% $CO_2$ (see FIGS. 6C and 6D).

Example 7

CD133$^+$ Osteosarcoma Cells Cultured in the HFB Proliferate and Upregulate the Expression of Proliferative Markers such as Ki-67

Figure 7:
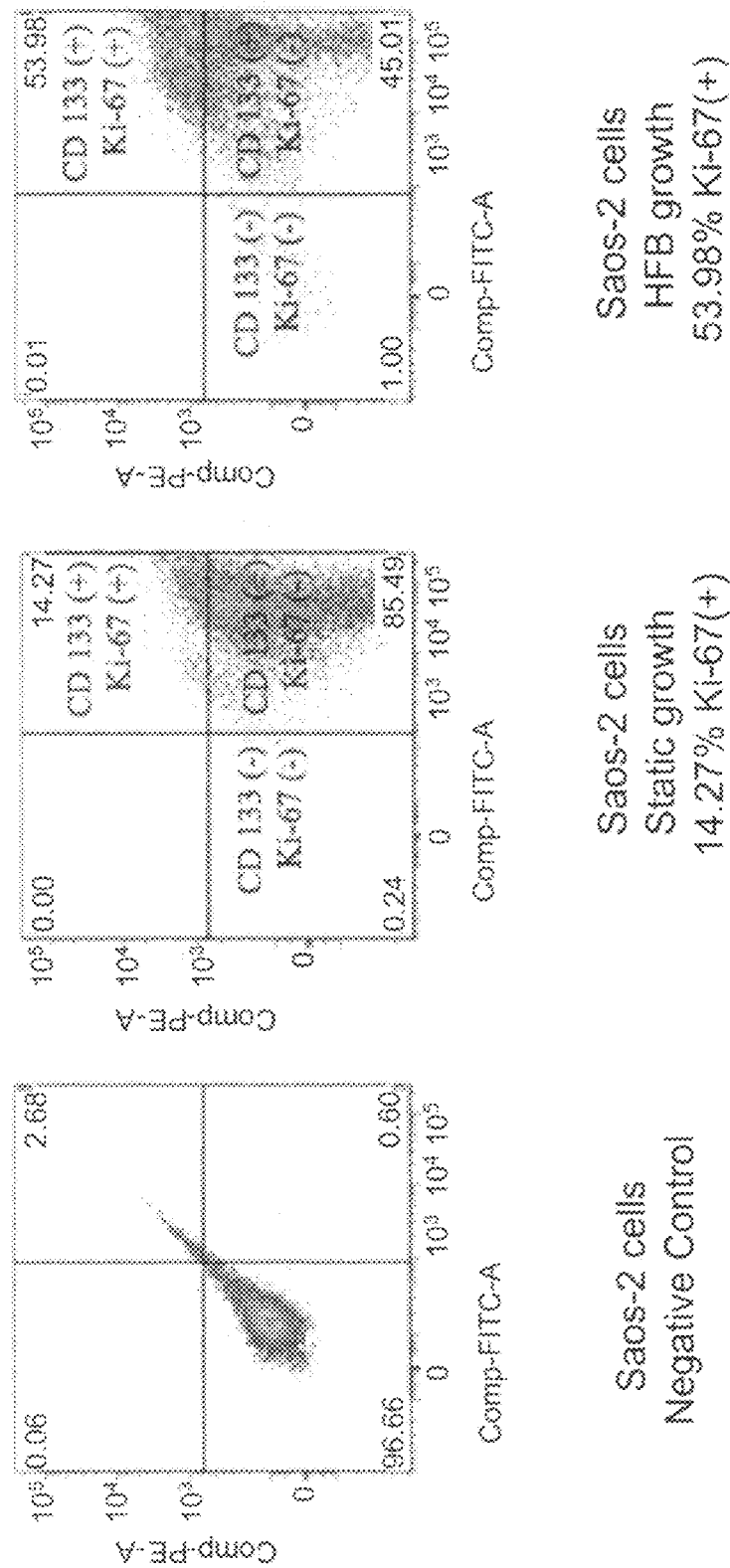
FIG. 7 shows flow cytometric analysis of SAOS-2 cells (7A), SAOS-2 cells grown under static growth conditions (7B) and SAOS-2 cells grown in the HFB for 5 days (7C) with the use of CD133 (stem cell marker) and Ki-67 (proliferation marker).

SAOS-2 cells were grown in the HFB as in Example 2 for 5 days or in adherent dishes under static conditions for 5 days, and their expression of CD133 and the proliferation marker, Ki-67 were measured by flow cytometry. The proliferation marker Ki-67 is expressed when mammalian cells are synthesizing DNA and it is typically used to demonstrate that cells are progressing through the S-phase of the cell cycle. The results show that compared to SAOS-2 cells grown in static conditions, a higher proportion of CD133$^+$ cells grown in HFB also express the proliferation marker Ki-67, showing that CD133$^+$ cells grown in HFB actually proliferate (see FIG. 7).

Example 8

Osteosarcoma Cells Grown in the HFB Display an Increase in Telomerase Activity

Figure 8:
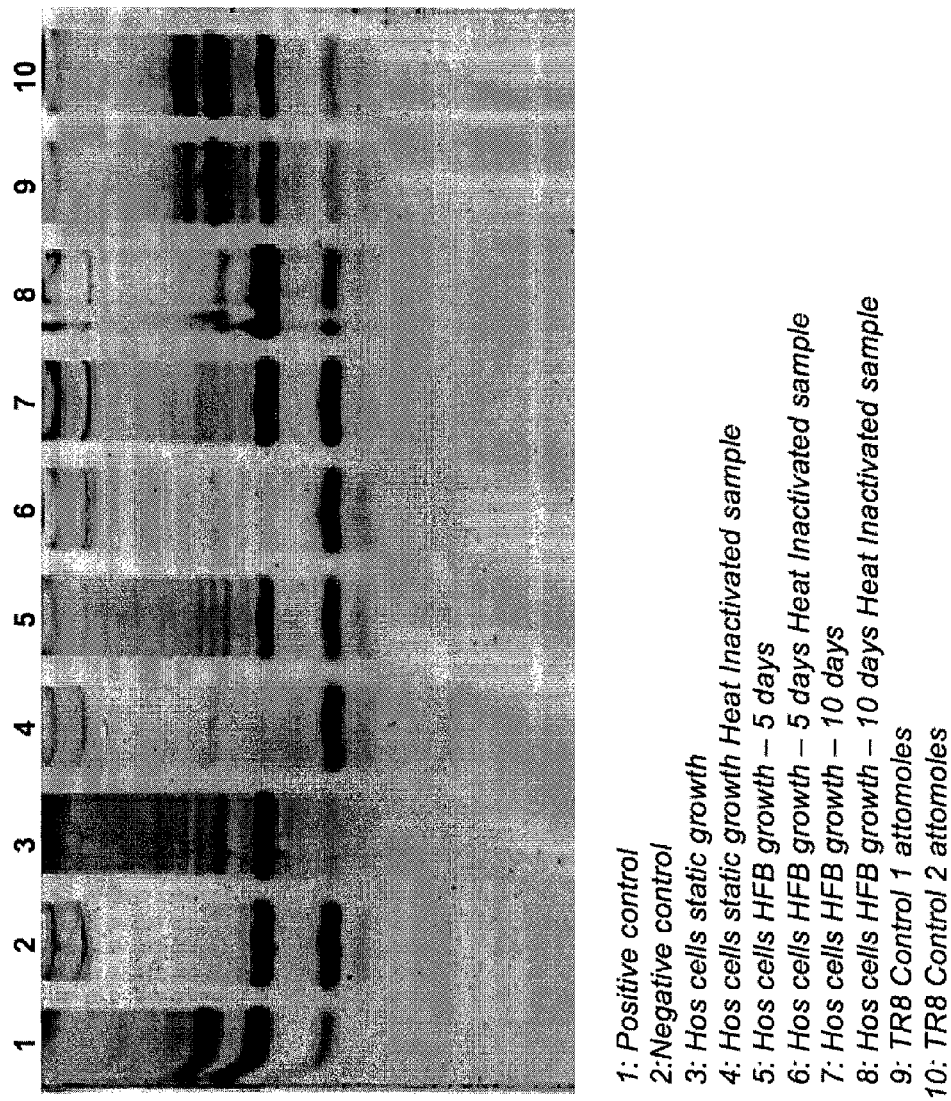
FIG. 8 shows a telomeric repeat amplification protocol (TRAP) assay comparing Hos osteosarcoma cells grown under static growth or in the HFB for 5 or 10 days.

Hos osteosarcoma cells (hTERT positive) were grown in HFB as in Example 2 for 5 (FIG. 8, lane 5) or 10 days (FIG. 8, lane 7) or under static conditions (FIG. 8, lane 3). CD133$^+$ enriched HOS osteosarcoma cells were seeded into a HFB at a concentration of $2.5 \times 10^5$ cells/mL medium. The rotational speed of the HFB was 25 rpm and the microgravitational force exerted by the HFB was 0.0174 g. The cells were grown in an incubator under these conditions: D-MEM medium containing 10% FBS, 1 mM L-Glutamine, 100 U/mL Penicillin, and 100 µg/mL of streptomycin was used at 37° C. and with 5% $CO_2$ for 5 or 10 days.

Telomerase activity in these cells was then measured by TRAP assay using the TRAPeze kit (Chemicon, Temecula, Calif.). The TRAP assay showed an enhancement of telomerase activity in the samples that were grown in HFB for 5 or 10 days compared to the cells grown in static conditions (see FIG. 8). As shown in FIG. 8, the samples cultured for 5 to 10 days in the HFB show an increased number of total products generated (TPG value) (lanes 5 and 7). Each unit of TPG (Total Product Generated) corresponds to the number of primers used in the reaction (TS primers in $1\times10^{-3}$ mole or 600 molecules) extended with at least 4 telomeric repeats by telomerase in the extract in a 30 minute incubation at 30° C. The assay has a linear range of 1 to 300 TPG, which is equivalent to telomerase activity from approximately 30 to 10,000 control cells.

The relative telomerase activity (RTA) level, i.e., the ratio between bands corresponding to amplified telomerase products and the internal standard (ITAS) at 0.5 µg protein extract was compared with values obtained using TRAP assay and the TRAPeze kit (Chemicon, Temecula, Calif.) on series of duplicate serial dilutions from individual CHAPS extracts. The RTA values of the samples treated with HFB for 5 to 10 days were higher than the controls.

Example 9

Osteosarcoma Cells Grown in HFB Display Increased Sensitivity to Cisplatin

Figure 9:
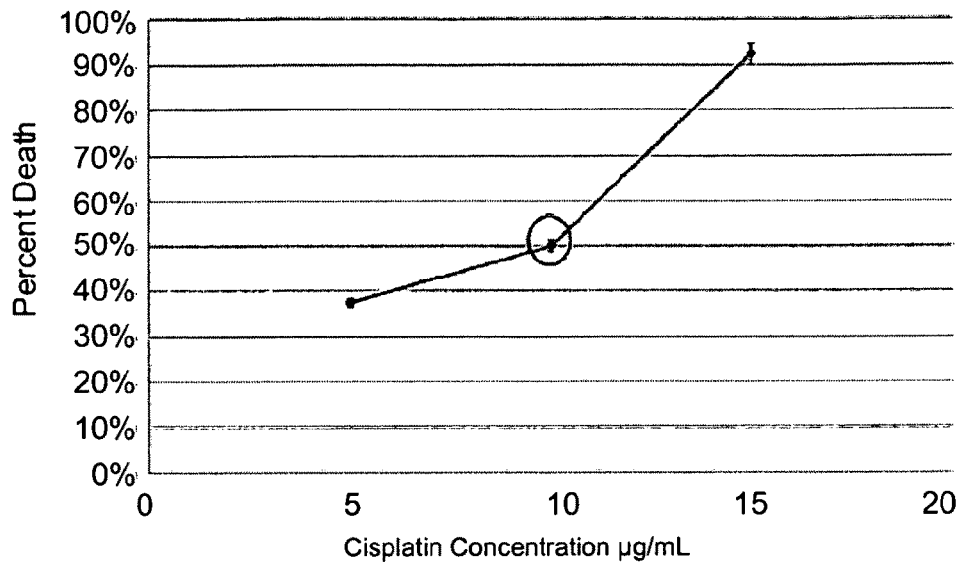
FIG. 9 shows the results of a chemo-sensitization procedure pertaining to the use of cisplatin.
Figure 9:
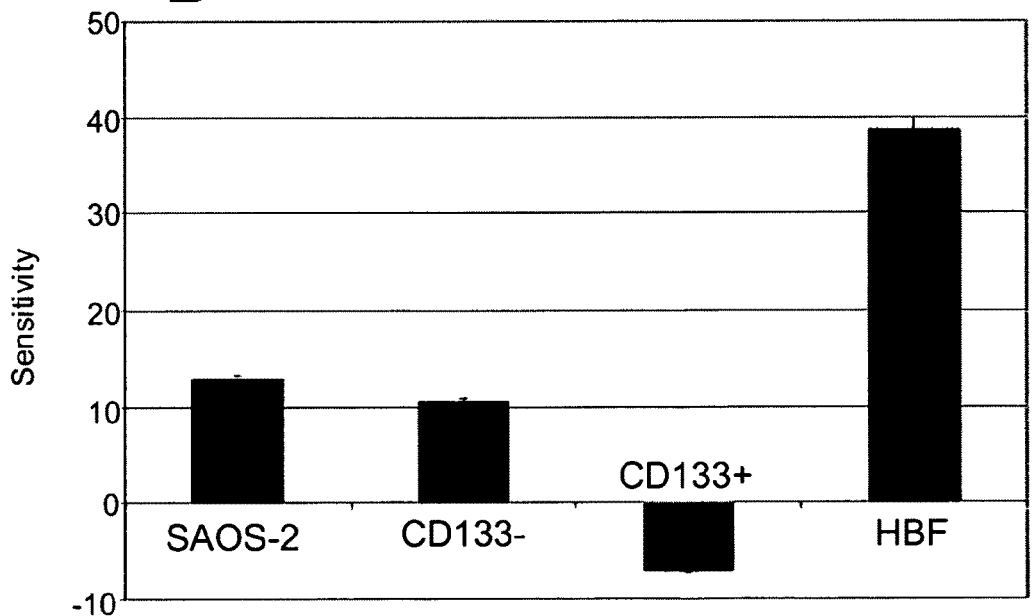
Figure 9:
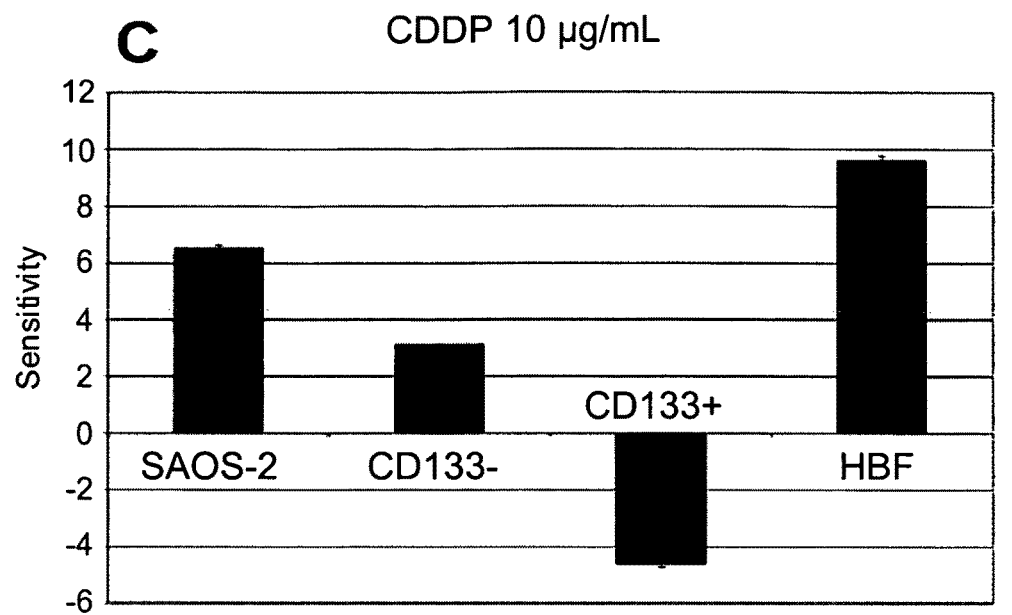
Figure 9:
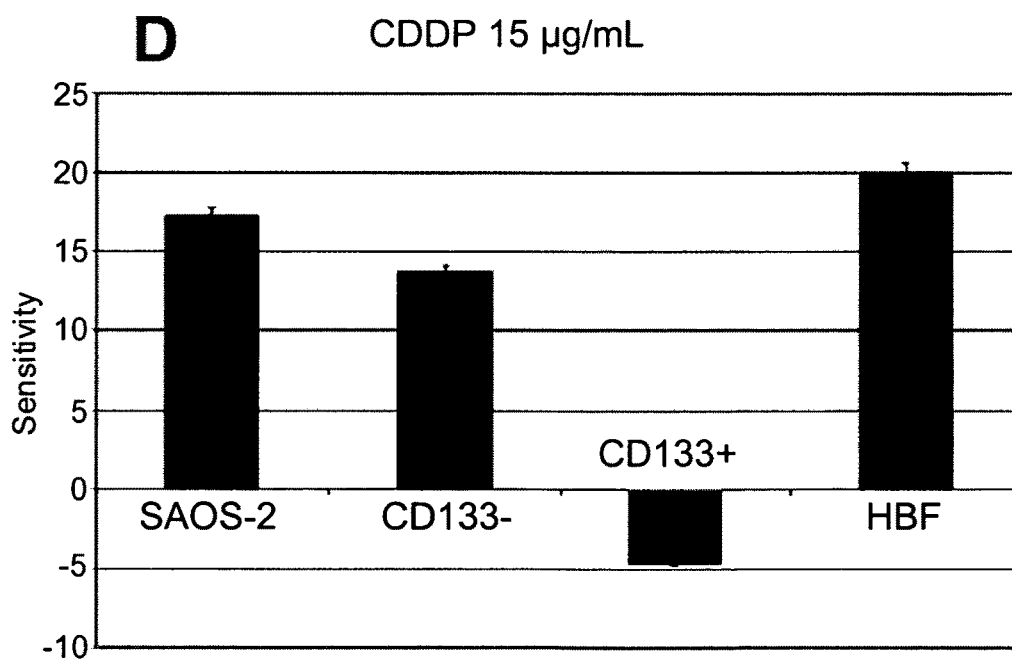

SAOS-2 cells were grown in HFB as in Example 2 for 5 days, and then harvested. $1\times10^4$ cells were plated in 96 well dishes and were subjected to 5 (FIG. 9B), 10 (FIG. 9C), or 15 (FIG. 9D) µg/mL of cisplatin for either 1 or 24 hours and then assayed 24 hours later for viability by [3-(4,5-dimethylthiazol-2-yl)-2,5-diphenyltetrazolium bromide] "MTT" assay. The results show that $CD133^+$ cells grown in HFB for 5 days were significantly more sensitive to cisplatin compared to whole SAOS-2 cultures, or $CD133^+$ or $CD133^-$ cells grown under normal gravity conditions (see FIG. 9). Specifically, $CD133^+$ cells were approximately 35, 4 and 15 fold more sensitive to cisplatin at the 5, 10 and 15 µg/mL doses, respectively, compared to resistant $CD133^+$ cells grown under normal gravity conditions. The SAOS-2 cell line was cultured in an incubator under these conditions: D-MEM medium containing 10% FBS, 1 mM L-Glutamine, 100 U/mL Penicillin, and 100 µg/mL of streptomycin, at 37° C. and with 5% $CO_2$.

Example 10

Osteosarcoma Cells Grown in HFB Display Increased Sensitivity to Methotrexate

Figure 10:
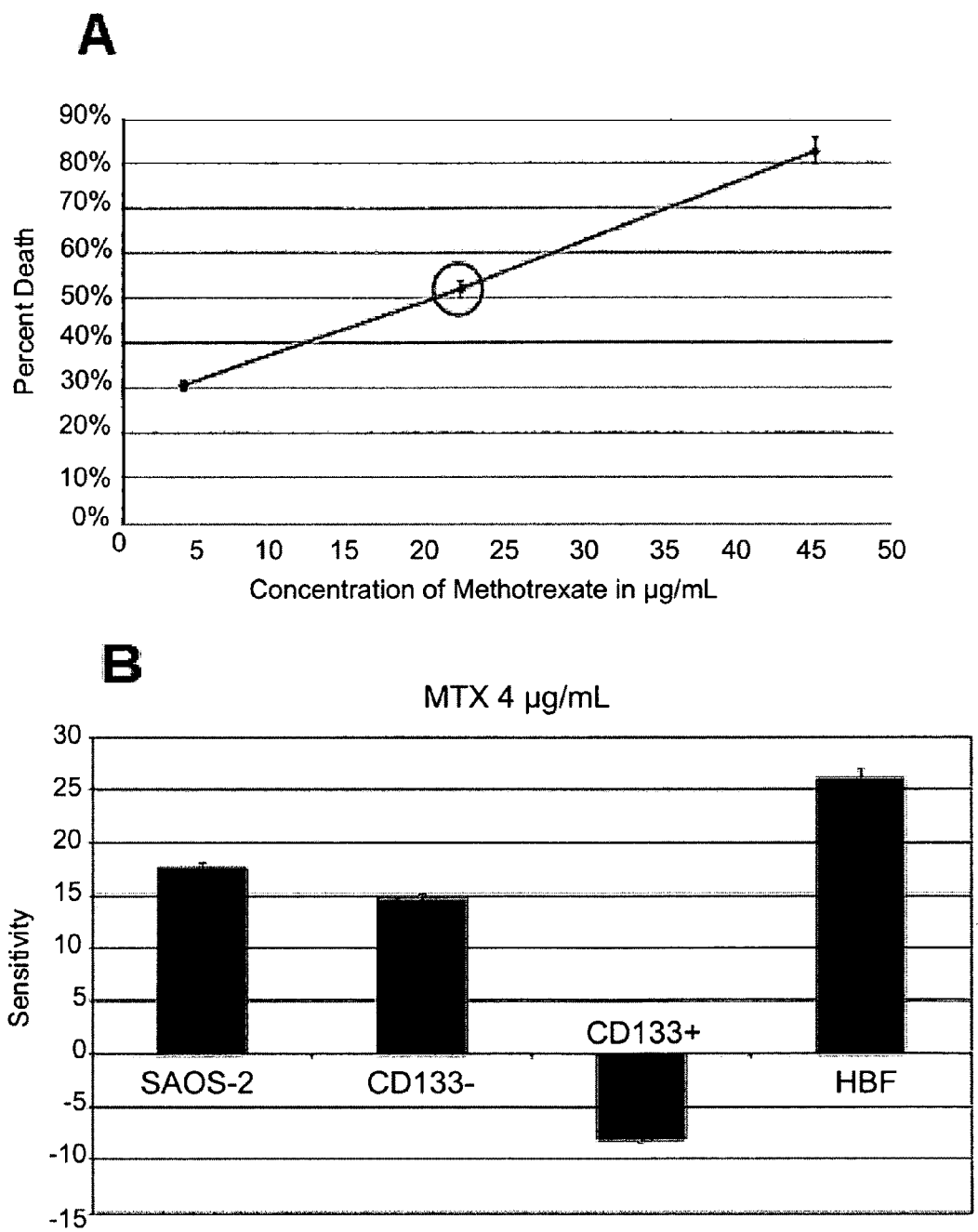
FIG. 10 shows the results of a chemo-sensitization procedure pertaining to the use of methotrexate.
Figure 10:
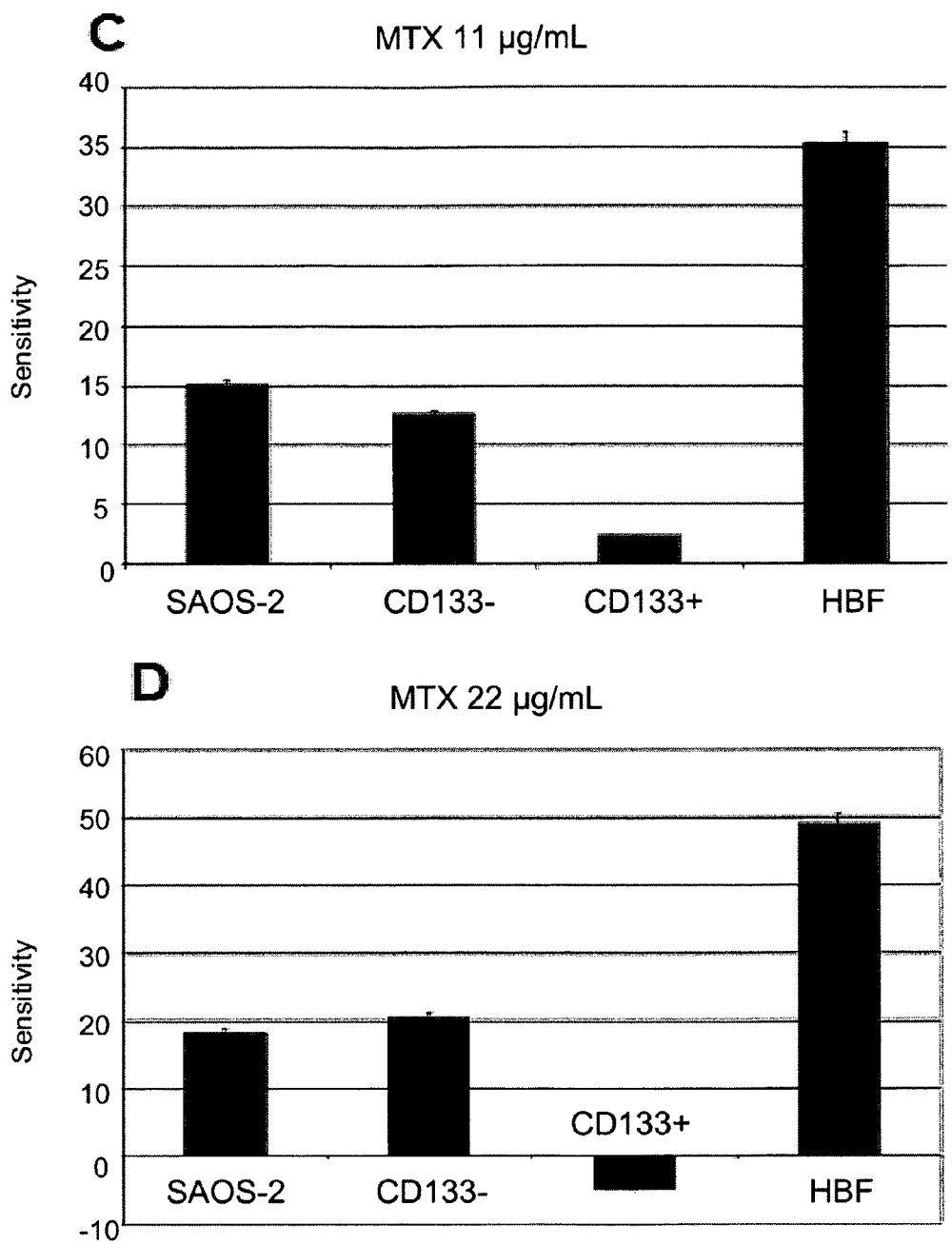
Figure 10:
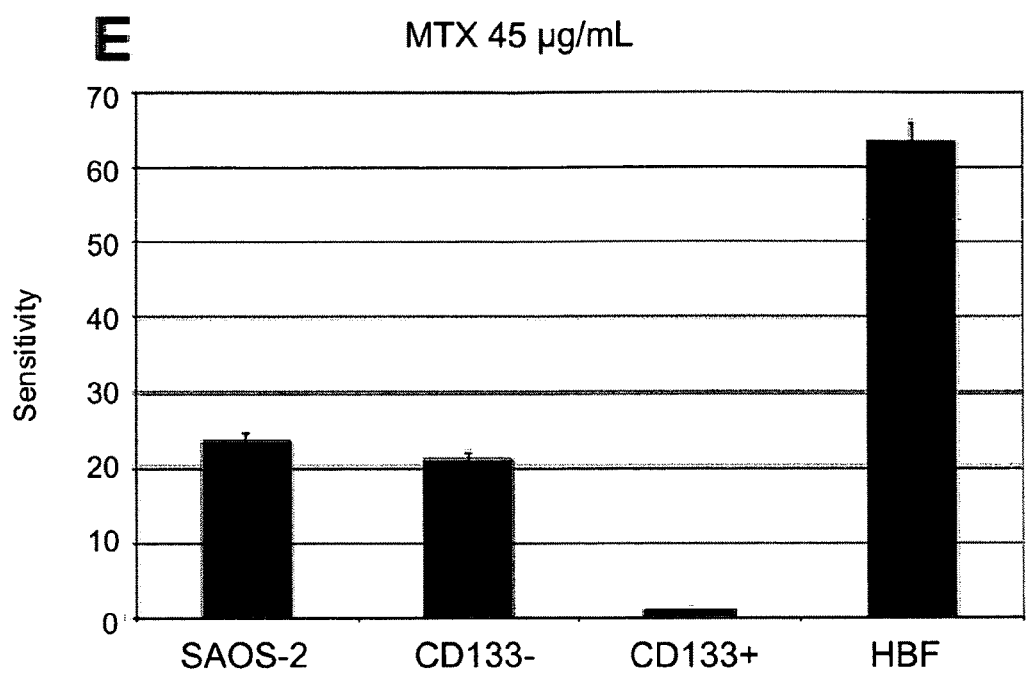

SAOS-2 cells were grown in HFB as in Example 2 for 5 days, and then harvested. $1\times10^4$ cells were plated in 96 well dishes and were subjected to 4 (FIG. 10B), 11 (FIG. 10C), 22 (FIG. 10D) or 45 (FIG. 10E) µg/mL of methotrexate for 1 or 24 hours and then assayed 24 hours later for viability by MTT assay. The results show that $CD133^+$ cells grown in HFB for 5 days were significantly more sensitive to methotrexate compared to whole SAOS-2 cultures, or $CD133^+$ or $CD133^-$ cells grown under normal gravity conditions (see FIG. 10). Specifically, $CD133^+$ cells were approximately 15, 35, 45 and 60 fold more sensitive to methotrexate at the 4, 11, 22 and 45 µg/mL doses, respectively, compared to resistant $CD133^+$ cells grown under normal gravity conditions. The SAOS-2 cell line was cultured in an incubator under these conditions: D-MEM medium containing 10% FBS, 1 mM L-Glutamine, 100 U/mL Penicillin, and 100 µg/mL of streptomycin, at 37° C. and with 5% $CO_2$.

Example 11

Osteosarcoma Cells Grown in HFB Display Increased Sensitivity to Doxorubicin

Figure 11:
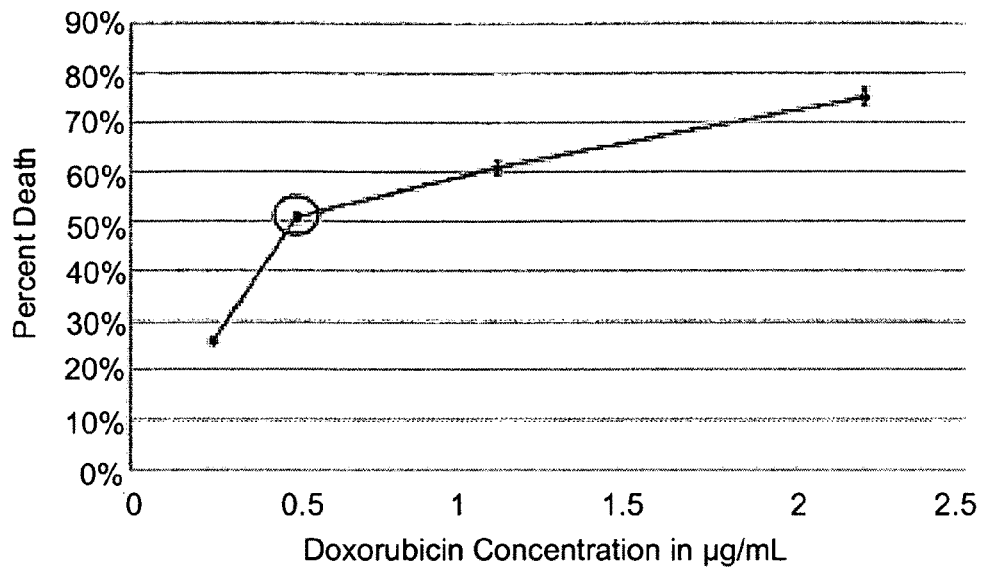
FIG. 11 shows the results of a chemo-sensitization procedure pertaining to the use of doxorubicin.
Figure 11:
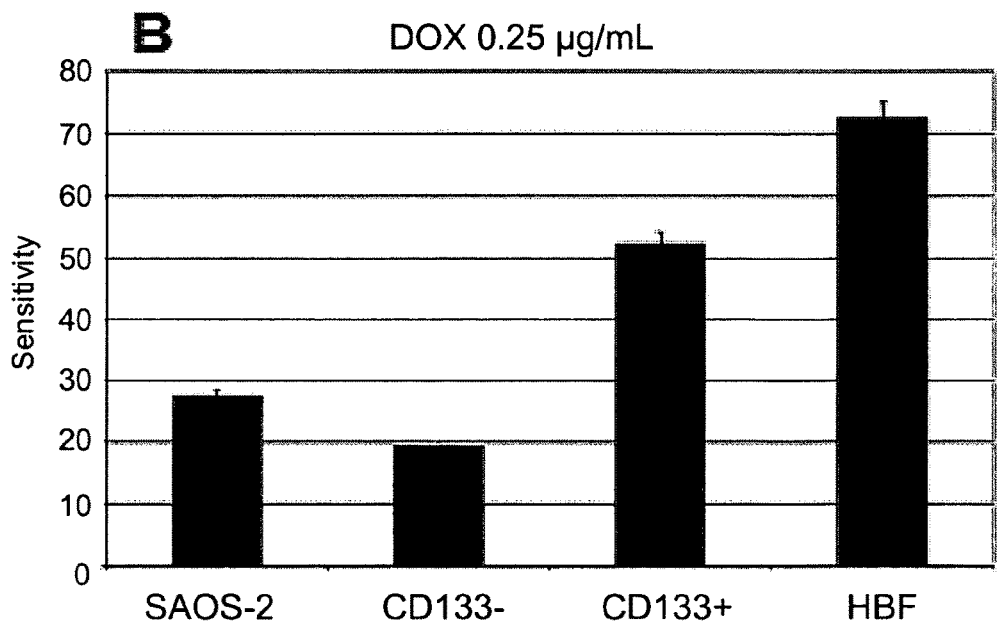
Figure 11:
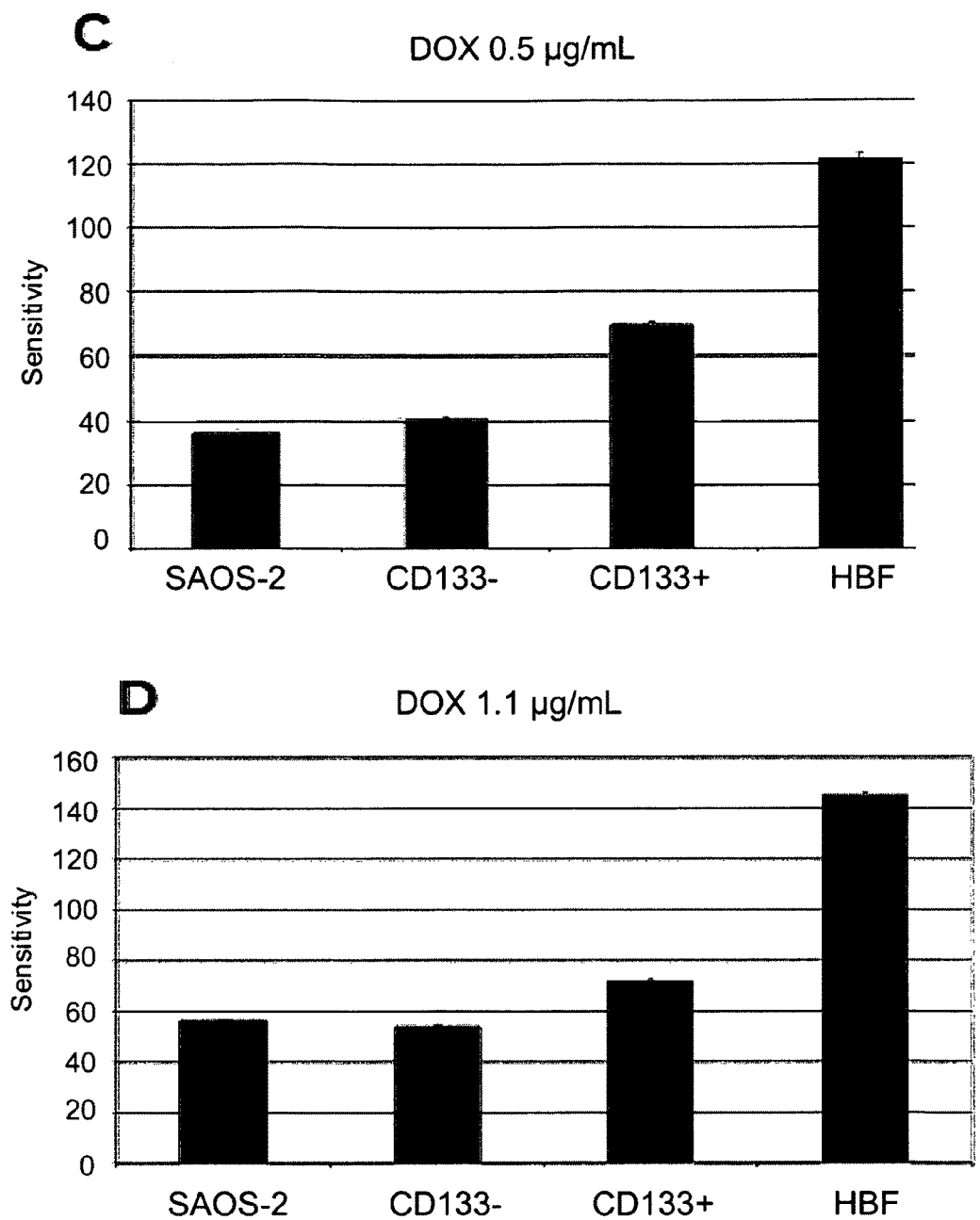
Figure 11:
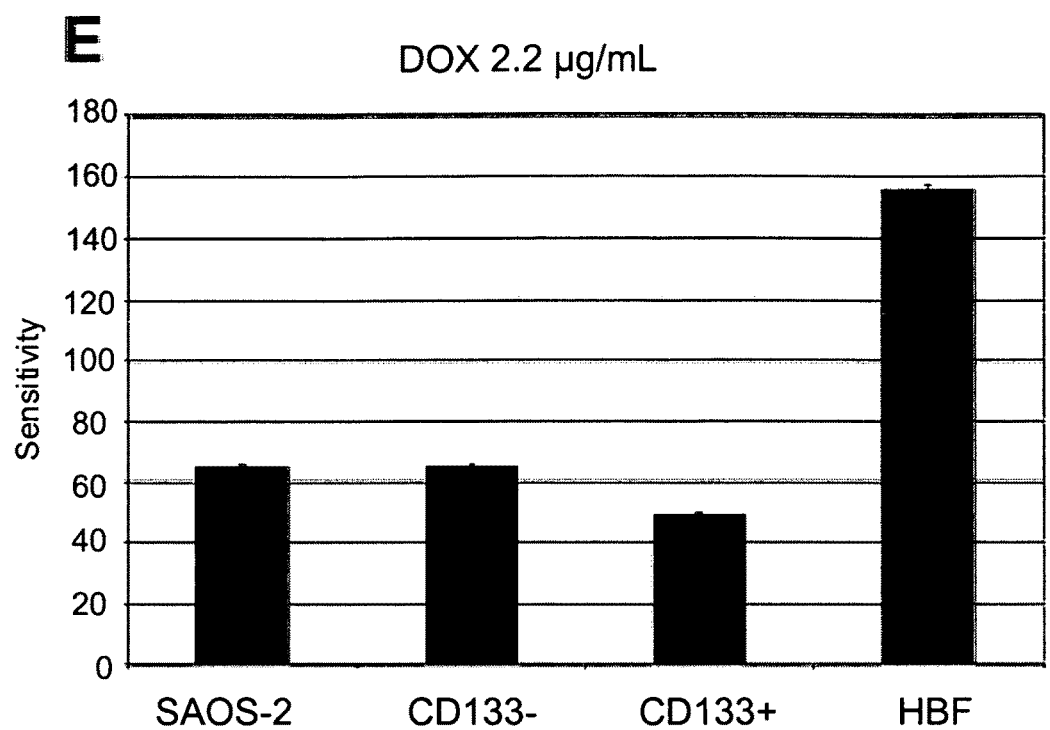

SAOS-2 cells were grown in HFB as in Example 2 for 5 days, and then harvested. $1\times10^4$ cells were plated in 96 well dishes and were subjected to 0.5 (FIG. 11B), 1.1 (FIG. 11C), or 2.5 (FIG. 11D) µg/mL of doxorubicin for 1 or 24 hours and then assayed 24 hours later for viability by MTT assay. The results show that $CD133^+$ cells grown in HFB for 5 days were significantly more sensitive to doxorubicin compared to whole SAOS-2 cultures, or $CD133^+$ or $CD133^-$ cells grown under normal gravity conditions (see FIG. 11). Specifically, $CD133^+$ cells were approximately 1.4, 2, and 2.3 fold more sensitive to doxorubicin at the 0.5, 1.1 and 2.5 µg/mL doses, respectively, compared to resistant $CD133^+$ cells grown under normal gravity conditions. The SAOS-2 line was cultured in an incubator under these conditions: D-MEM medium containing 10% FBS, 1 mM L-Glutamine, 100 U/mL Penicillin, and 100 µg/mL of streptomycin, at 37° C. and with 5% $CO_2$.

Example 12

Figure 12:
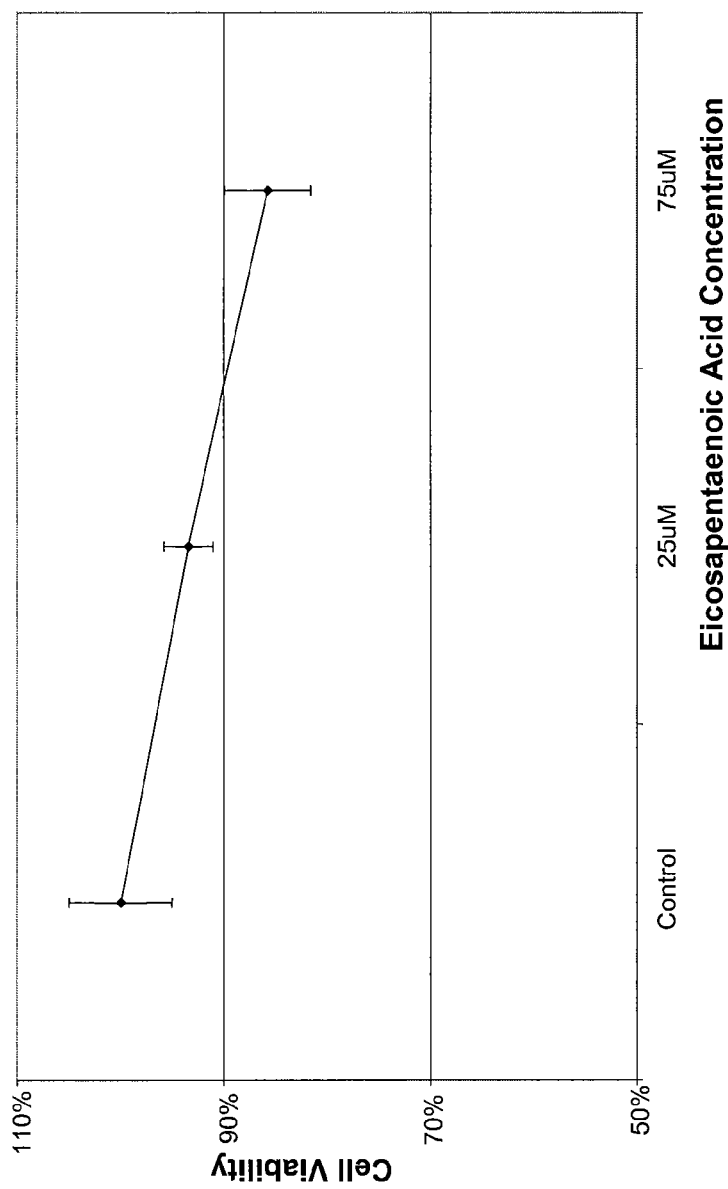
FIG. 12 shows the results of a viability assay of SAOS-2 cells grown in the presence of omega-3 fatty acids.

The Viability of Osteosarcoma Cells Grown in Normal Gravity (1 G) in the Presence of Omega-3 Fatty Acids is Decreased SAOS-2 cells grown in normal gravity (1G) condition, containing a mixed population of CD133 (−) and CD133(+) cells, were harvested and $1\times10^4$ cells were plated in 96 well dishes and were treated with 25 or 75 µM of eicosapentaenoic acid (MP Biomedicals, Solon, Ohio) for 4 days and then assayed 24 hours later for viability by MTT assay. The control is 75 µM ethanol. The results show that the viability of SAOS-2 cells grown in the presence of 75 µM omega-3 fatty acids was decreased (see FIG. 12).

$3\times10^5$ SAOS-2 cells were plated in 6-well dishes and were treated with 25 or 75 µM of eicosapentaenoic acid (MP Biomedicals, Solon, Ohio) for 4 days and then assayed 24 hours later for Annexin-V. Annexin-V is a cellular protein in the annexin group that is used to detect apoptosis. The results show that the viability of SAOS-2 cells grown in the presence of omega-3 fatty acids in normal gravity was decreased (see Table 1). Thus, addition of omega-3 fatty acids kills cancer cells.

TABLE 1

Percentage of SAOS Cells Cultured with Eicosapentaenoic acid

|  | Live | Early Apoptotic | Apoptotic Necrotic | Necrotic |
|---|---|---|---|---|
| Control | 92.4 | 3.9 | 2.5 | 1.2 |
| 25 µM Eicosapentaenoic acid | 82.7 | 10 | 6.3 | 1 |
| 75 µM Eicosapentaenoic acid | 72.6 | 14.5 | 11.1 | 1.7 |

Example 13

The Growth of CD133(+) SAOS-2 Cells in the HFB is Increased in the Presence of Omega-3 Fatty Acids Six×10$^6$ SAOS-2 cells were grown in HFB for 3 days, which selected for CD133(+) cells, and then 75 μM of eicosapentaenoic acid (MP Biomedicals, Solon, Ohio) or 75 μM of ethanol (as a control) were added on day 3 and the cells were grown for two more days in HFB. On day 5, cells were removed from the HFB, counted and subjected to flow cytometry (99.8% purity).

TABLE 2

Cell Count of CD133(+) SAOS Cells

| SAOS in HFB | Cell Count |
| --- | --- |
| +75 μM Eicosapentaenoic acid | 4,560,000 |
| +75 μM Ethanol | 2,280,000 |

Figure 13:
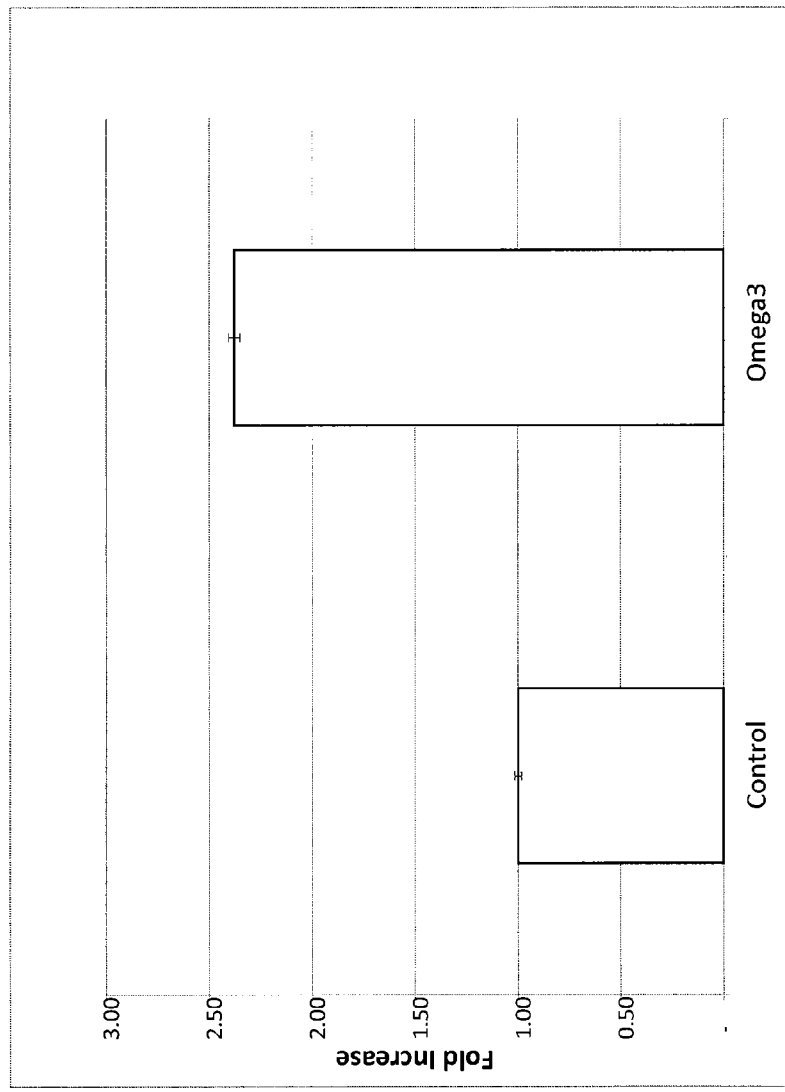
FIG. 13 shows the results of a growth assay of CD133(+) SAOS-2 cells grown in the presence or absence of omega-3 fatty acids.

The results show that SAOS-2 cells grown in HFB in the presence of eicosapentaenoic acid grow at a faster rate (see Table 2 and FIG. 13).

Example 14

Figure 14:
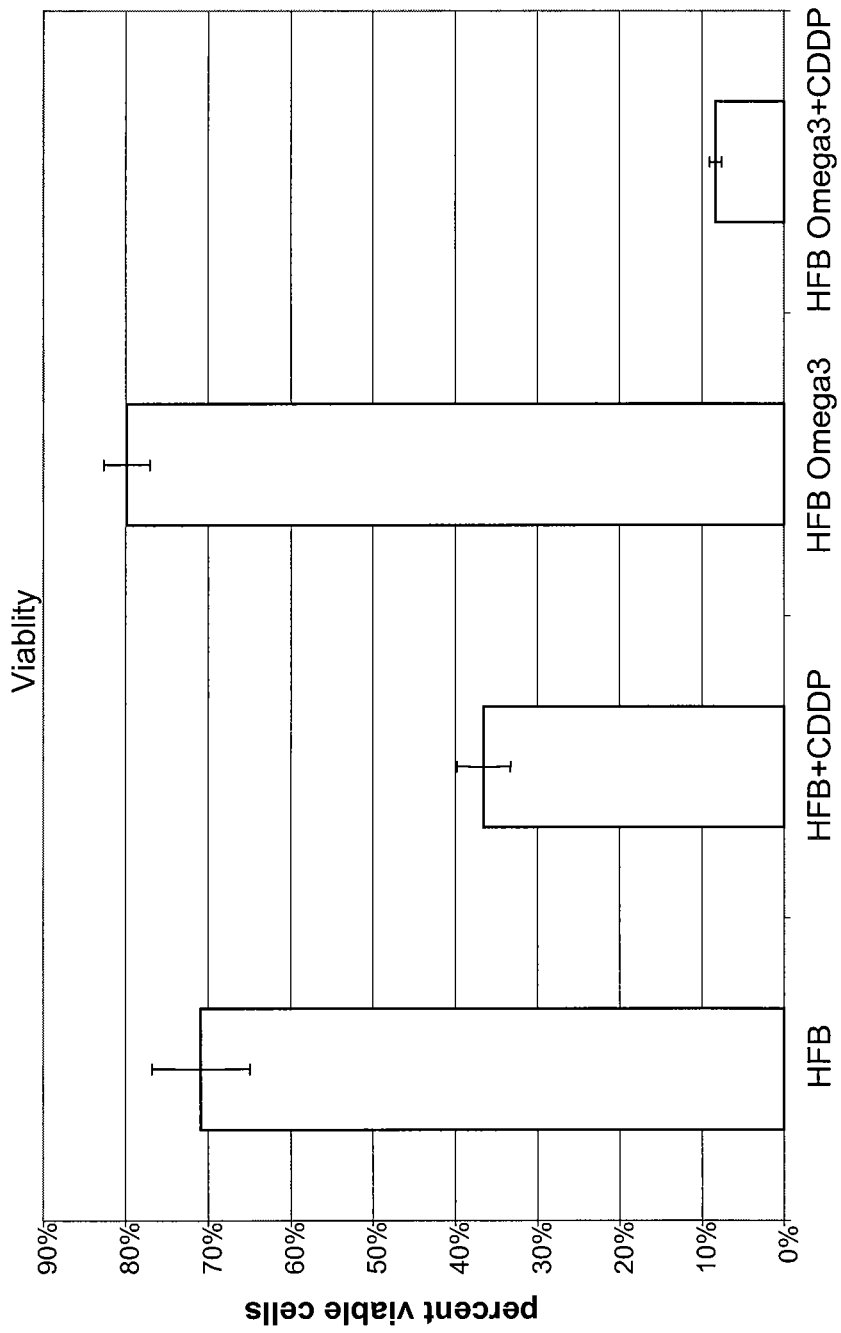
FIG. 14 shows the results of a viability assay of CD133(+) SAOS-2 cells grown in the presence or absence of omega-3 fatty acids and/or cisplatin. HFB indicates that the cells were grown in a Hydrodynamic Focusing Bioreactor (HFB). CDDP indicates that the cells were treated with cisplatin. Omega3 indicates that the cells were treated with omega-3 fatty acids.

The Viability of Cells Grown in HFB in the Presence of Omega-3 fatty acids and Cisplatin is Reduced Six×10$^6$ SAOS-2 cells were grown in HFB for 3 days, which selected for CD133(+) cells, and then 75 μM of eicosapentaenoic acid (MP Biomedicals, Solon, Ohio) or 75 μM of ethanol (as a control) were added on day 3 and the cells were grown for two more days in HFB. On day 5, cells were removed from the HFB, counted and subjected to flow cytometry (99.8% purity). One×10$^4$ cells were plated in 96 well dishes with or without 5 μg/mL of Cisplatin and with or without 75 μM of eicosapentaenoic acid for 24 hours. An MTT assay was performed in triplicate to assess cell viability (see FIG. 14). The cells were also assayed for the presence of Annexin-V (see Table 3).

TABLE 3

Percentage of viable, apoptotic and necrotic SAOS Cells Cultured in the HFB with or without Eicosapentaenoic acid and with or without Cisplatin

|  | Live | Early Apoptotic | Apoptotic Necrotic | Necrotic |
| --- | --- | --- | --- | --- |
| SAOS in HFB | 49.9 | 35.1 | 13.6 | 1.4 |
| SAOS in HFB + Cisplatin | 44.1 | 40.4 | 12.7 | 2.8 |
| SAOS in HFB + Eicosapentaenoic acid | 67.4 | 16 | 8.6 | 7.9 |
| SAOS in HFB + Cisplatin + Eicosapentaenoic acid | 47.1 | 24.8 | 20.7 | 7.4 |

The results show that CD133 (+) SAOS-2 cells grown in HFB in the presence of eicosapentaenoic acid grow at a faster rate and display more sensitivity to treatment with cisplatin than cells grown in the absence of omega-3 fatty acids.

What is claimed is:

1. A method for increasing telomere length in stem cells comprising: seeding said stem cells into a Hydrodynamic Focusing Bioreactor (HFB), culturing said stem cells under conditions allowing for telomere growth, isolating said stem cells, and determining the telomere length.

2. The method of claim 1 wherein use of said HFB leads to a low shear environment with a maximum shear force at 10 rpm of about 0.01 dyne/cm$^2$.

3. The method of claim 1 wherein said telomeres are lengthened by about 6-24 repeats as compared to stem cells grown in normal gravity conditions.

4. A method for increasing telomerase activity in stem cells comprising: seeding said stem cells into a Hydrodynamic Focusing Bioreactor (HFB), culturing said stem cells under conditions allowing for increased telomerase activity, isolating said stem cells, and determining the telomerase activity.

5. The method of claim 4 wherein use of said HFB leads to a low shear environment with a maximum shear force at 10 rpm of about 0.01 dyne/cm$^2$.

6. A method for increasing the life span of stem cells comprising: seeding said stem cells into a Hydrodynamic Focusing Bioreactor (HFB), culturing said stem cells under conditions allowing for increased life span, isolating said stem cells, and determining the telomerase activity in said stem cells, wherein an increase in telomerase length is indicative of increased life span.

7. The method of claim 6 wherein the telomeres of said stem cells are lengthened.

8. The method of claim 6 wherein use of said HFB leads to a low shear environment with a maximum shear force at 10 rpm of about 0.01 dyne/cm$^2$.

9. A method for selectively enriching a stem cell population comprising:
    seeding a heterogeneous population of cells into a Hydrodynamic Focusing Bioreactor (HFB), the heterogeneous population of cells including one or more stem cells and one or more differentiated cells; and
    culturing said heterogeneous population of cells under microgravity conditions in the HFB for a period of time sufficient to selectively kill the one or more differentiated cells and selectively enrich the one or more stem cells to thereby selectively enrich the stem cell population.

10. The method of claim 9 wherein the microgravitational force exerted by said HFB is between about 0.01 to about 0.99 g.

11. The method of claim 10 wherein the micro gravitational force exerted by said HFB is about 0.01 g.

12. The method of claim 9 wherein the enriched cell population is CD133$^+$.

13. The method of claim 9 wherein the enriched cell population comprises adult stem cells.

14. The method of claim 9 wherein the enriched cell population comprises cancer stem cells.

15. The method of claim 9 wherein said stem cells are embryonic stem cells.

16. The method of claim 9 wherein said stem cells are grown at a temperature of about 35° C. to about 39° C.

17. The method of claim 16 wherein said stem cells are grown at a temperature of about 37° C.

18. The method of claim 9 wherein said stem cells are cultured in said HFB for about 1 to about 35 days.

19. The method of claim 18 wherein said stem cells are cultured in said HFB for about 7 days.

20. The method of claim 9 wherein said stem cells are cultured at an initial concentration of about 0.0005 to about 1.0×10$^6$ cells per ml medium.

21. The method of claim 20 wherein said stem cells are cultured at an initial concentration of about 2.5×10$^5$ cells per ml medium.

22. The method of claim 9 wherein the rotational speed of said HFB is from about 1 to about 30 rpm.

23. The method of claim 22 wherein the rotational speed of said HFB is about 25 rpm.

24. The method of claim 9 wherein said stem cells are derived from a cancer patient.

25. The method of claim 24 wherein said cancer patient has a cancer selected from the group consisting of liquid tumor and solid organ tumor.

26. The method of claim 9 wherein said stem cells are derived from a healthy patient.

27. The method of claim 9 wherein said stem cells are genetically modified.

28. The method of claim 9 wherein use of said HFB leads to a low shear environment with a maximum shear force at 10 rpm of about 0.01 dyne/cm$^2$.

29. The method of claim 9 wherein said stem cells are cultured in a culture medium comprising from about 0 to about 20 percent serum, about 1 mM L-Glutamine, 100 U/mL penicillin, and 100 ug/mL Streptomycin.

30. A method for culturing stem cells comprising: seeding said stem cells into a Hydrodynamic Focusing Bioreactor (HFB) and culturing said stem cells under conditions allowing for telomere growth.

31. A method for culturing stem cells comprising: seeding said stem cells into a Hydrodynamic Focusing Bioreactor (HFB) and culturing said stem cells under conditions allowing for increased telomerase activity.

32. A method for culturing stem cells comprising: seeding said stem cells into a Hydrodynamic Focusing Bioreactor (HFB) and culturing said stem cells under conditions allowing for increased life span.

33. A method for proliferating cancer cells comprising seeding cancer cells into a Hydrodynamic Focusing Bioreactor (HFB) culturing said cancer cells, and allowing said cancer cells to form into cancerous tissue.

34. The method of claim 33 wherein said cancer cells are cultured in the presence of omega-3 fatty acids.

* * * * *